United States Patent [19]
Slassi et al.

[11] Patent Number: 6,100,291
[45] Date of Patent: *Aug. 8, 2000

[54] PYRROLIDINE-INDOLE COMPOUNDS HAVING 5-HT$_6$ AFFINITY

[75] Inventors: Abdelmalik Slassi; Louise Edwards, both of Mississauga; Anne O'Brien, Toronto; Tao Xin, North York; Ashok Tehim, Mississauga, all of Canada

[73] Assignee: Allelix Biopharmaceuticals Inc., Mississauga, Canada

[*] Notice: This patent issued on a continued prosecution application filed under 37 CFR 1.53(d), and is subject to the twenty year patent term provisions of 35 U.S.C. 154(a)(2).

[21] Appl. No.: 09/039,269

[22] Filed: Mar. 16, 1998

[51] Int. Cl.$^7$ .................... A61K 31/404; C07D 403/06
[52] U.S. Cl. ............................. 514/414; 548/468
[58] Field of Search .............................. 548/468; 514/414

[56] References Cited

U.S. PATENT DOCUMENTS

| | | | |
|---|---|---|---|
| 3,481,953 | 12/1969 | Herbst | 260/326 |
| 3,489,429 | 1/1970 | Herbst | 260/326 |
| 3,489,770 | 1/1970 | Herbst | 260/326 |
| 4,021,431 | 5/1977 | Zenitz | 260/293 |
| 4,870,085 | 9/1989 | Glaser et al. | 514/323 |
| 5,066,660 | 11/1991 | Oxford et al. | 514/323 |
| 5,532,237 | 7/1996 | Gallant et al. | 514/235.2 |

FOREIGN PATENT DOCUMENTS 0 815 861   6/1997   European Pat. Off. .

OTHER PUBLICATIONS

International Publication No. WO 90/05721 published May 31, 1990.
International Publication No. WO 92/13856 published Aug. 20, 1992.
International Publication No. WO 95/32966 published Dec. 7, 1995.
International Publication No. WO 96/25397 published Aug. 22, 1996.
International Pubilcation No. WO 97/47302 published Dec. 18, 1997.
Taylor et al., Molecular Pharmacology, 34; 1988, pp. 42–53, "Molecular Determinants for Recognition of RU 24969 Analogs at Central 5–Hydroxytryptamine Recognition Sites...".
Zheng et al., Tetrahedron Letters, 34, 1993, pp. 2235–2238, "Vinylation of the Indole 3–Position Via Palladium–Catalyzed Cross–Coupling".
Zheng et al., Heterocycles, 37, 1994, pp. 1761–1772, "Palladium Catalyzed Cross–Coupling Reaction between 3–Indole Boronic Acids and Tetrahydropyridine Triflates".
JP Abstract 05043544, Feb. 23, 1993.

*Primary Examiner*—Patricia L. Morris
*Attorney, Agent, or Firm*—Arent Fox Kintner Plotkin & Kahn, PLLC

[57] ABSTRACT

Described herein are compounds with affinity for the 5-HT$_6$ receptor, which have the general formula:

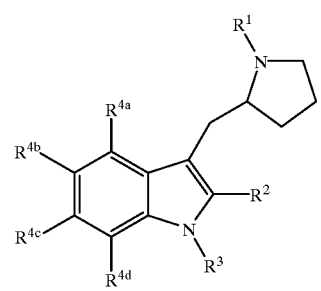

wherein:

$R^1$ is selected from the group consisting of H and $C_{1-4}$alkyl;

$R^2$ is selected from the group consisting of H, $C_{1-4}$alkyl and benzyl;

$R^3$ is selected from the group consisting of $COR^5$, $SO_2R^5$, $CONHC_{1-4}$alkyl and $C(S)SR^6$;

$R^{4a}$ is selected from the group consisting of H, OH, halo, $C_{1-4}$alkyl and $C_{1-4}$alkoxy;

$R^{4b}$ is selected from the group consisting of H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl;

$R^{4c}$ is selected from the group consisting of H, OH, halo, $C_{1-4}$alkyl and $C_{1-4}$alkoxy;

$R^{4d}$ is selected from the group consisting of H, OH, halo, $C_{1-4}$alkyl and $C_{1-4}$alkoxy;

$R^5$ is selected from the group consisting of phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—; and $R^6$ is selected from $C_{1-4}$alkyl, allyl, propargyl and optionally substituted benzyl wherein the benzyl group is optionally substituted with 1–4 substituents selected from cyano, $C_{1-4}$alkyl and halo.

Also described is the use of these compounds as pharmaceuticals to treat indications where inhibition of the 5-HT$_6$ receptor is implicated, such as schizophrenia.

23 Claims, No Drawings

PYRROLIDINE-INDOLE COMPOUNDS HAVING 5-HT$_6$ AFFINITY

This invention relates to indole compounds having affinity for the serotonin 5-HT$_6$ receptor, to pharmaceutical compositions containing them and to their medical use, particularly in the treatment of CNS conditions.

According to one aspect of the invention, there are provided compounds of Formula I and salts, solvates or hydrates thereof:

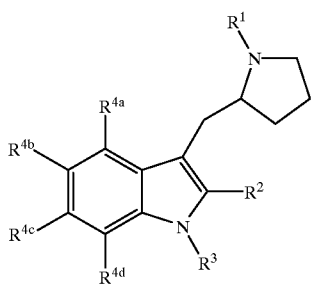

I wherein:
- $R^1$ is selected from the group consisting of H and $C_{1-4}$alkyl;
- $R^2$ is selected from the group consisting of H, $C_{1-4}$alkyl and benzyl;
- $R^3$ is selected from the group consisting of $COR^5$, $SO_2R^5$, $CONHC_{1-4}$alkyl and $C(S)SR^6$;
- $R^{4a}$ is selected from the group consisting of H, OH, halo, $C_{1-4}$alkyl and $C_{1-4}$alkoxy;
- $R^{4b}$ is selected from the group consisting of H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl;
- $R^{4c}$ is selected from the group consisting of H, OH, halo, $C_{1-4}$alkyl and $C_{1-4}$alkoxy;
- $R^{4d}$ is selected from the group consisting of H, OH, halo, $C_{1-4}$alkyl and $C_{1-4}$alkoxy;
- $R^5$ is selected from the group consisting of phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—; and
- $R^6$ is selected from $C_{1-4}$alkyl, allyl, propargyl and optionally substituted benzyl wherein the benzyl group is optionally substituted with 1–4 substituents selected from cyano, $C_{1-4}$alkyl and halo.

According to another aspect of the invention, there is provided a pharmaceutical composition comprising a compound of Formula I in an amount effective to antagonize the 5-HT$_6$ receptor, and a pharmaceutically acceptable carrier.

In another aspect of the present invention there are provided compositions containing the present compounds in amounts for pharmaceutical use to treat CNS conditions where a 5-HT$_6$ ligand is indicated, for example, for the treatment or prevention of central nervous system disturbances such as psychosis, schizophrenia, manic depression, depression, neurological disturbances, memory disturbances, Parkinsonism, amylotrophic lateral sclerosis, Alzheimer's disease and Huntington's disease. These and other aspects of the present invention are described in greater detail hereinbelow.

DETAILED DESCRIPTION AND PREFERRED EMBODIMENTS

The term "$C_{1-4}$alkyl" as used herein means straight and branched chain alkyl radicals containing from one to four carbon atoms and includes methyl, ethyl, propyl, isopropyl, t-butyl and the like.

The term "$C_{1-4}$alkoxy" as used herein means straight and branched chain alkoxy radicals containing from one to four carbon atoms and includes methoxy, ethoxy, propyloxy, isopropyloxy, t-butoxy and the like.

The term "cycloalkyloxy" as used herein means saturated carbocyclooxy radicals containing from 3–7 carbon atoms and includes cyclopropyloxy, cyclohexyloxy and the like.

The term "1,2-methylenedioxy" as used herein means "—O—CH$_2$—O—" attached to adjacent nodes of a ring.

The term halo as used herein means halogen and includes fluoro, chloro, bromo and the like.

The term "pharmaceutically acceptable salt" means either an acid addition salt or a basic addition salt which is compatible with the treatment of patients.

A "pharmaceutically acceptable acid addition salt" is any non-toxic organic or inorganic acid addition salt of the base compounds represented by Formula I or any of its intermediates. Illustrative inorganic acids which form suitable salts include hydrochloric, hydrobromic, sulfuric and phosphoric acid and acid metal salts such as sodium monohydrogen orthophosphate and potassium hydrogen sulfate. Illustrative organic acids which form suitable salts include the mono-, di- and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic, p-toluenesulfonic acid and other sulfonic acids such as methanesulfonic acid and 2-hydroxyethanesulfonic acid. Either the mono- or di-acid salts can be formed, and such salts can exist in either a hydrated, solvated or substantially anhydrous form. In general, the acid addition salts of these compounds are more soluble in water and various hydrophilic organic solvents, and generally demonstrate higher melting points in comparison to their free base forms.

A "pharmaceutically acceptable basic addition salt" is any non-toxic organic or inorganic base addition salt of the acid compounds represented by Formula I or any of its intermediates. Illustrative inorganic bases which form suitable salts include lithium, sodium, potassium, calcium, magnesium or barium hydroxides. Illustrative organic bases which form suitable salts include aliphatic, alicyclic or aromatic organic amines such as methylamine, trimethyl amine and picoline or ammonia. The selection of the appropriate salt may be important so that an ester functionality elsewhere in the molecule is not hydrolyzed. The selection criteria for the appropriate salt will be known to one skilled in the art.

"Solvate" means a compound of Formula I or the pharmaceutically acceptable salt of a compound of Formula I wherein molecules of a suitable solvent are incorporated in a crystal lattice. A suitable solvent is physiologically tolerable at the dosage administered as the solvate. Examples of suitable solvents are ethanol and the like.

The term "stereoisomers" is a general term for all isomers of the individual molecules that differ only in the orientation of their atoms in space. It includes mirror image isomers (enantiomers), geometric (cis/trans) isomers and isomers of compounds with more than one chiral centre that are not mirror images of one another (diastereomers).

The term "treat" or "treating" means to alleviate symptoms, eliminate the causation of the symptoms either on a temporary or permanent basis, or to prevent or slow the appearance of symptoms of the named disorder or condition.

The term "therapeutically effective amount" means an amount of the compound which is effective in treating the named disorder or condition.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to the patient. One example of such a carrier is a pharmaceutically acceptable oil typically used for parenteral administration.

The term "schizophrenia" means schizophrenia, schizophreniform, disorder, schizoaffective disorder and psychotic disorder wherein the term "psychotic" refers to delusions, prominent hallucinations, disorganized speech or disorganized or catatonic behavior. See Diagnostic and Statistical Manual of Mental Disorder, fourth edition, American Psychiatric Association, Washington, D.C.

The present invention includes within its scope prodrugs of the compounds of Formula I. In general, such prodrugs will be functional derivatives of the compounds of Formula I which are readily convertible in vivo into the required compound of Formula I. Conventional procedures for the selection and preparation of suitable prodrug derivatives are described, for example, in "Design of Prodrugs" ed. H. Bundgaard, Elsevier, 1985.

In embodiments of the invention, compounds of Formula I include those in which $R^1$ is selected from H and $C_{1-4}$alkyl. Preferably, $R^1$ is methyl. Also within the scope of the invention are compounds of Formula I wherein $R^2$ is selected from H, $C_{1-4}$alkyl and benzyl. In preferred embodiments, $R^2$ is H.

Compounds of the invention include Formula I compounds wherein $R^3$ is selected from $COR^5$, $SO_2R^5$, $CONHC_{1-4}$alkyl and $C(S)SR^6$. In preferred embodiments $R^3$ is selected from $COR^5$ and $SO_2R^5$. Within $R^3$, $R^5$ is selected from phenyl, pyridyl, thienyl, quinolinyl and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS— and $R^6$ is selected from $C_{1-4}$alkyl, allyl, propargyl and optionally substituted benzyl wherein the benzyl group is optionally substituted with 1–4 substituents selected from cyano, $C_{1-4}$alkyl and halo. Specifically, $R^5$ is selected from phenyl and thienyl optionally substituted with 1–3 groups selected from methyl, methoxy, fluoro, chloro and 1,2-methylenedioxy, and $R^6$ is selected from methyl, propargyl, benzyl and p-cyanobenzyl. In preferred embodiments, $R^5$ is selected from phenyl, p-methylphenyl, p-fluorophenyl, p-methoxyphenyl, o-chlorophenyl, o-methoxyphenyl, and thienyl and $R^6$ is methyl.

In further embodiments of the invention, $R^{4b}$ is selected from H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl. In specific embodiments, $R^{4b}$ is selected from H, fluoro, cyclohexyloxy, hydroxy, benzyloxy, phenoxy, chloro, bromo and methyl. Preferably $R^{4b}$ is selected from chloro, cyclohexyloxy and fluoro.

In other embodiments of the invention, $R^{4a}$, $R^{4c}$ and $R^{4d}$ are each independently selected from H, OH, halo, $C_{1-4}$alkyl and $C_{1-4}$alkoxy. In a further embodiment, $R^{4a}$ and $R^{4c}$ are both H and $R^{4d}$ is halo. In a preferred embodiment, $R^{4a}$, $R^{4c}$ and $R^{4d}$ are all H.

In embodiments of the invention, the compounds of Formula I include:

5-Cyclohexyloxy-3-(1-methyl-2-pyrrolidinylmethyl)-1-phenylsulfonylindole;

2-Benzyl-5-hydroxy-3-(1-methyl-2-pyrrolidinylmethyl)-1-phenylsulfonylindole;

5-Hydroxy-3-(1-methyl-2-pyrrolidinylmethyl)-1-phenylsulfonylindole;

3-(1-Methyl-2-pyrrolidinylmethyl)-1-phenylsulfonylindole;

1-(4-Methoxyphenylsulfonyl)-3-(1-methyl-2-pyrrolidinylmethyl)indole;

5-Chloro-3-(1-methyl-2-pyrrolidinylmethyl)-1-phenylsulfonylindole;

5-Chloro-1-(4-methoxyphenylsulfonyl)-3-(1-methyl-2-pyrrolidinylmethyl)indole;

5-Chloro-1-(4-fluorophenylsulfonyl)-3-(1-methyl-2-pyrrolidinylmethyl)indole;

1-Benzoyl-3-(1-methyl-2-pyrrolidinylmethyl)indole;

1-(4-Methoxybenzoyl)-3-(1-methyl-2-pyrrolidinylmethyl)indole;

1-(4-Fluorobenzoyl)-3-(1-methyl-2-pyrrolidinylmethyl)indole;

1-(2-Chlorobenzoyl)-5-cyclohexyloxy-3-(1-methyl-2-pyrrolidinylmethyl)indole;

5-Cyclohexyloxy-1-(2-methoxybenzoyl)-3-(1-methyl-2-pyrrolidinylmethyl)indole;

5-Cyclohexyloxy-1-(4-methoxybenzoyl)-3-(1-methyl-2-pyrrolidinylmethyl)indole;

5-Cyclohexyloxy-1-(3,4-methylenedioxybenzoyl)-3-(1-methyl-2-pyrrolidinylmethyl)indole;

5-Cyclohexyloxy-1-(2,6-dichlorobenzoyl)-3-(1-methyl-2-pyrrolidinylmethyl)indole;

5-Cyclohexyloxy-3-(1-methyl-2-pyrrolidinylmethyl)-1-(2-thienoyl)indole;

1-Benzoyl-5-bromo-3-(1-methyl-2-pyrrolidinylmethyl)indole;

1-Benzoyl-5-chloro-3-(1-methyl-2-pyrrolidinylmethyl)indole;

5-Chloro-1-(4-methoxybenzoyl)-3-(1-methyl-2-pyrrolidinylmethyl)indole;

5-Chloro-1-(4-fluorobenzoyl)-3-(1-methyl-2-pyrrolidinylmethyl)indole;

5-Cyclohexyloxy-3-(1-methyl-2-pyrrolidinylmethyl)-1-(S-methylxanthyl)indole;

5-Cyclohexyloxy-3-(1-methyl-2-pyrrolidinylmethyl)-1-[S-(4-cyanobenzyl)xanthyl]indole;

5-Cyclohexyloxy-3-(1-methyl-2-pyrrolidinylmethyl)-1-(S-benzylxanthyl)indole;

5-Methyl-3-(1-methyl-2-pyrrolidinylmethyl)-1-(S-methylxanthyl)indole;

5-Fluoro-3-(1-methyl-2-pyrrolidinylmethyl)-1-(S-methylxanthyl)indole;

1-(S-Benzylxanthyl)-5-fluoro-(1-methyl-2-pyrrolidinylmethyl)indole;

1-(S-Allylxanthyl)-5-fluoro-3-(1-methyl-2-pyrrolidinylmethyl)indole;

5-Fluoro-3-(1-methyl-2-pyrrolidinylmethyl)-1-(S-propargylxanthyl)indole;

3-(1-Methyl-2-pyrrolidinylmethyl)-1-(S-methylxanthyl) indole;

1-(S-Benzylxanthyl)-3-(1-methyl-2-pyrrolidinylmethyl) indole;

1-(S-Allylxanthyl)-3-(1-methyl-2-pyrrolidinylmethyl) indole;

5-Cyclohexyloxy-3-(1-methyl-2-pyrrolidinylmethyl)-1-benzoylindole;

5-Cyclohexyloxy-3-(1-methyl-2-pyrrolidinylmethyl)-1-(4-methoxyphenylsulfonyl)indole;

5-Benzyloxy-3-(1-methyl-2-pyrrolidinylmethyl)-1-(N-methylcarboxamido)indole;

5-Hydroxy-3-(1-methyl-2-pyrrolidinylmethyl)-1-(N-methylcarboxamido)indole;

1-Phenylsulfonyl-5-hydroxy-3-(1-methyl-2-pyrrolidinylmethyl)indole; and

1-Phenylsulfonyl-5-phenoxy-3-(1-methyl-2-pyrrolidinylmethyl)indole.

In specific embodiments of the invention, the compounds of Formula I include:

5-Cyclohexyloxy-3-(1-methyl-2-pyrrolidinylmethyl)-1-phenylsulfonylindole;

2-Benzyl-5-hydroxy-3-(1-methyl-2-pyrrolidinylmethyl)-1-phenylsulfonylindole;

5-Hydroxy-3-(1-methyl-2-pyrrolidinylmethyl)-1-phenylsulfonylindole;

3-(1-Methyl-2-pyrrolidinylmethyl)-1-phenylsulfonylindole;

1-(4-Methoxyphenylsulfonyl)-3-(1-methyl-2-pyrrolidinylmethyl)indole;

5-Chloro-3-(1-methyl-2-pyrrolidinylmethyl)-1-phenylsulfonylindole;

5-Chloro-1-(4-methoxyphenylsulfonyl)-3-(1-methyl-2-pyrrolidinylmethyl)indole;

5-Chloro-1-(4-fluorophenylsulfonyl)-3-(1-methyl-2-pyrrolidinylmethyl)indole;

1-Benzoyl-3-(1-methyl-2-pyrrolidinylmethyl)indole;

1-(4-Methoxybenzoyl)-3-(1-methyl-2-pyrrolidinylmethyl)indole;

1-(4-Fluorobenzoyl)-3-(1-methyl-2-pyrrolidinylmethyl) indole;

1-(2-Chlorobenzoyl)-5-cyclohexyloxy-3-(1-methyl-2-pyrrolidinylmethyl)indole;

5-Cyclohexyloxy-1-(2-methoxybenzoyl)-3-(1-methyl-2-pyrrolidinylmethyl)indole;

5-Cyclohexyloxy-1-(4-methoxybenzoyl)-3-(1-methyl-2-pyrrolidinylmethyl)indole;

5-Cyclohexyloxy-1-(3,4-methylenedioxybenzoyl)-3-(1-methyl-2-pyrrolidinylmethyl)indole;

5-Cyclohexyloxy-1-(2,6-dichlorobenzoyl)-3-(1-methyl-2-pyrrolidinylmethyl)indole;

5-Cyclohexyloxy-3-(1-methyl-2-pyrrolidinylmethyl)-1-(2-thienoyl)indole;

1-Benzoyl-5-bromo-3-(1-methyl-2-pyrrolidinylmethyl) indole;

1-Benzoyl-5-chloro-3-(1-methyl-2-pyrrolidinylmethyl) indole;

5-Chloro-1-(4-methoxybenzoyl)-3-(1-methyl-2-pyrrolidinylmethyl)indole;

5-Chloro-1-(4-fluorobenzoyl)-3-(1-methyl-2-pyrrolidinylmethyl)indole;

5-Cyclohexyloxy-3-(1-methyl-2-pyrrolidinylmethyl)-1-benzoylindole;

5-Cyclohexyloxy-3-(1-methyl-2-pyrrolidinylmethyl)-1-(4-methylphenylsulfonyl)indole;

1-Phenylsulfonyl-5-hydroxy-3-(1-methyl-2-pyrrolidinylmethyl)indole; and

1-Phenylsulfonyl-5-phenoxy-3-(1-methyl-2-pyrrolidinylmethyl)indole.

In more specific embodiments of the invention, the compounds of Formula I include:

5-Cyclohexyloxy-3-(1-methyl-2-pyrrolidinylmethyl)-1-phenylsulfonylindole;

3-(1-Methyl-2-pyrrolidinylmethyl)-1-phenylsulfonylindole;

1-(4-Methoxyphenylsulfonyl)-3-(1-methyl-2-pyrrolidinylmethyl)indole;

5-Chloro-3-(1-methyl-2-pyrrolidinylmethyl)-1-phenylsulfonylindole;

5-Chloro-1-(4-methoxyphenylsulfonyl)-3-(1-methyl-2-pyrrolidinylmethyl)indole;

5-Chloro-1-(4-fluorophenylsulfonyl)-3-(1-methyl-2-pyrrolidinylmethyl)indole;

1-Benzoyl-3-(1-methyl-2-pyrrolidinylmethyl)indole;

1-(4-Methoxybenzoyl)-3-(1-methyl-2-pyrrolidinylmethyl)indole;

1-(4-Fluorobenzoyl)-3-(1-methyl-2-pyrrolidinylmethyl) indole;

1-(2-Chlorobenzoyl)-5-cyclohexyloxy-3-(1-methyl-2-pyrrolidinylmethyl)indole;

5-Cyclohexyloxy-1-(2-methoxybenzoyl)-3-(1-methyl-2-pyrrolidinylmethyl)indole;

5-Cyclohexyloxy-1-(4-methoxybenzoyl)-3-(1-methyl-2-pyrrolidinylmethyl)indole;

5-Cyclohexyloxy-3-(1-methyl-2-pyrrolidinylmethyl)-1-(2-thienoyl)indole;

1-Benzoyl-5-bromo-3-(1-methyl-2-pyrrolidinylmethyl) indole;

1-Benzoyl-5-chloro-3-(1-methyl-2-pyrrolidinylmethyl) indole;

5-Chloro-1-(4-methoxybenzoyl)-3-(1-methyl-2-pyrrolidinylmethyl)indole;

5-Chloro-1-(4-fluorobenzoyl)-3-(1-methyl-2-pyrrolidinylmethyl)indole;

5-Cyclohexyloxy-3-(1-methyl-2-pyrrolidinylmethyl)-1-benzoylindole;

5-Cyclohexyloxy-3-(1-methyl-2-pyrrolidinylmethyl)-1-(4-methylphenylsulfonyl)indole; and 1-Phenylsulfonyl-5-phenoxy-3-(1-methyl-2-pyrrolidinylmethyl)indole.

In the most specific embodiments of the invention, the compounds of Formula I include:

1-(2-Chlorobenzoyl)-5-cyclohexyloxy-3-(1-methyl-2-pyrrolidinylmethyl)indole;

5-Chloro-3-(1-methyl-2-pyrrolidinylmethyl)-1-phenylsulfonylindole; and

5-Chloro-1-(4-fluorobenzoyl)-3-(1-methyl-2-pyrrolidinylmethyl)indole.

Acid addition salts of the compounds of Formula I are most suitably formed from pharmaceutically acceptable acids, and include for example those formed with inorganic acids e.g. hydrochloric, sulphuric or phosphoric acids and organic acids e.g. succinic, maleic, acetic or fumaric acid. Other non-pharmaceutically acceptable salts e.g. oxalates may be used for example in the isolation of compounds of Formula I for laboratory use, or for subsequent conversion to a pharmaceutically acceptable acid addition salt. Also included within the scope of the invention are solvates and hydrates of the invention.

The conversion of a given compound salt to a desired compound salt is achieved by applying standard techniques, in which an aqueous solution of the given salt is treated with a solution of base e.g. sodium carbonate or potassium hydroxide, to liberate the free base which is then extracted into an appropriate solvent, such as ether. The free base is then separated from the aqueous portion, dried, and treated with the requisite acid to give the desired salt.

All of the compounds of the present invention have at least one chiral centre. The invention extends to cover all structural and optical isomers of the various compounds, as well as racemic mixtures thereof.

In accordance with other aspects of the invention, the compounds of the present invention can be prepared by processes analogous to those established in the art. For example, as shown in Scheme 1, compounds of Formula I may be prepared by first treating compounds of Formula A, wherein $R^1$ is $C_{1-4}$alkyl and $R^2$ and $R^{4a-d}$ are as defined in Formula I, with an appropriate base, followed by the addition of a reagent which will provide one of the various functional groups defined by $R^3$ in Formula I. Therefore, for example, treatment of compounds of Formula A with a strong base such as lithium diisopropylamide, n-butyllithium or sodium bis(trimethylsilyl)amide in an inert solvent such as tetrahydrofuran or hexanes at a temperature in the range of −100 to 0° C. or, alternatively an organic amine in the presence of dimethylaminopyridine (DMAP), in an inert solvent such as methylene chloride or chloroform, at a temperature in the range of 0–60° C., followed by the addition of acid chlorides of Formula B or sulfonyl chlorides of Formula C, wherein $R^5$ is as defined in Formula I, provides compounds of Formula I wherein $R^3$ is $COR^5$ or $SO_2R^5$ respectively. Preferred conditions are sodium bis(trimethylsilyl)amide in tetrahydrofuran at −78° C. followed by warming to room temperature or triethylamine and DMAP in methylene chloride at room temperature. In a similar fashion, compounds of Formula A can be treated with strong base such as lithium diisopropylamide, n-butylliithium or sodium bis(trimethylsilyl)amide, in an inert solvent such as tetrahydrofuran or hexanes, at a temperature in the range of −100–30° C., followed by the addition carbon disulfide and then a reagent of Formula D, wherein X is an appropriate leaving group such as halo, preferably bromo or iodo, and $R^6$ is as defined in Formula I, to provide compounds of Formula I wherein $R^3$ is $C(S)SR^6$. Preferred reaction conditions include sodium bis(trimethylsilyl)amide in tetrahydrofuran at −78° C. followed by warming to room temperature. Compounds of Formula I wherein $R^3$ is $CONHC_{1-4}$alkyl may be prepared by treating compounds of Formula A with a base such as triethylamine or potassium carbonate in the presence of isocyanates of Formula E in an inert solvent such as methylene chloride, acetonitrile, toluene or chloroform and at temperatures in the range of 0–120° C. Preferred conditions include triethylamine in toluene at 110° C. Reagents B, C, D and E are commercially available or can be prepared using standard methods known to those skilled in the art. The preparation of compounds of Formula A is described below.

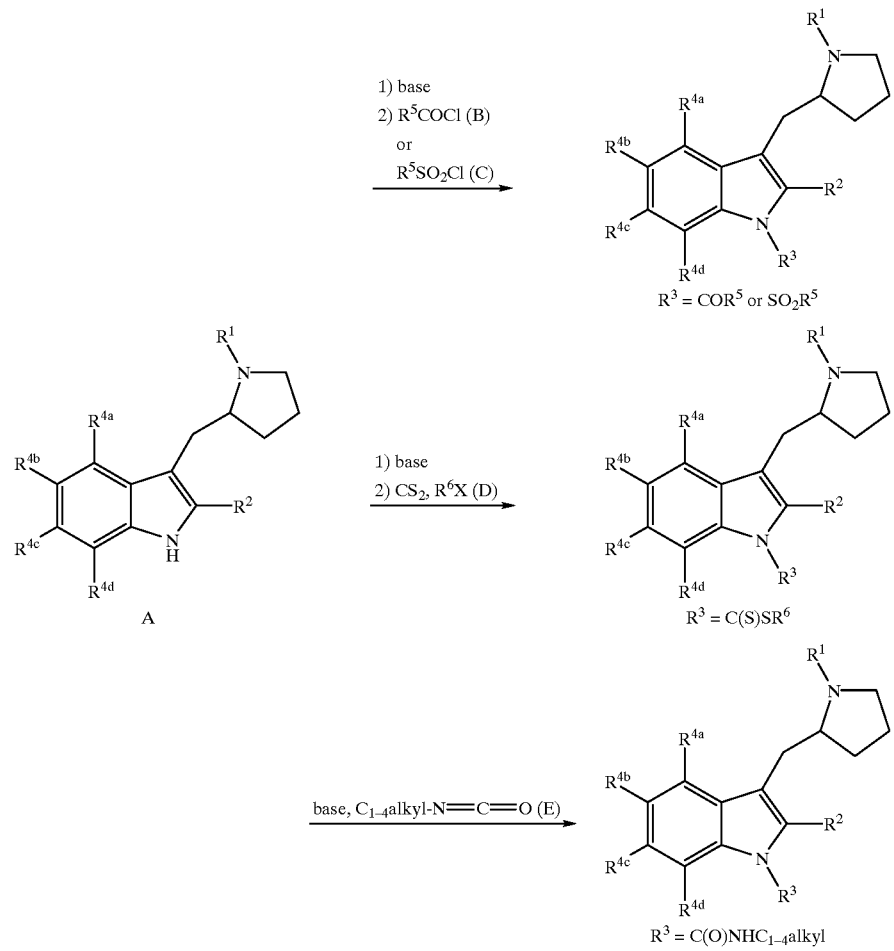

Compounds of Formula I wherein $R^1$ is H may be prepared by treating a compound of Formula A, wherein $R^1$ is a suitable protecting group such as t-butoxycarbonyl (t-BOC), with reagents of Formula A, B, C, D (and $CS_2$) and E as described above. Removal of the protecting group may be performed under standard conditions, for example using acidic conditions such as HCl in ethyl acetate to remove the t-BOC group, to provide compounds of Formula I wherein $R^1$ is H.

Compounds of Formula I, wherein $R^2$ is selected from $C_{1-4}$alkyl and benzyl, $R^1$ is $C_{1-4}$alkyl and $R^3$ and $R^{4a-d}$ are as defined in Formula I, may also be prepared by treating compounds of Formula I, wherein $R^2$ is H, $R^1$ is selected from $C_{1-4}$alkyl and $R^3$ and $R^{4a-d}$ are as defined in Formula I, with a strong base, such as n-butyllithium, in an inert solvent, such as tetrahydrofuran, at a temperature in the range of $-100-0°$ C. (preferably $-78°$ C.), followed by the addition of a reagent of formula $R^2$—X, wherein $R^2$ is selected from $C_{1-4}$alkyl and benzyl and X is a suitable leaving group such as bromo, followed by warming to room temperature. The above reaction may also be carried out on a compound of Formula I, wherein $R^2$ is selected from $C_{1-4}$alkyl and benzyl, $R^1$ is a suitable protecting group, such as t-butoxycarbonyl, and $R^3$ and $R^{4a-d}$ are as defined in Formula I, which, after removal of the protecting group using standard deprotection conditions (for example HCl in ethyl acetate to remove the t-butoxycarbonyl protecting group), provides a compound of Formula I wherein $R^2$ is selected from $C_{1-4}$alkyl and benzyl, $R^1$ is H and R and $R^{4a-c}$ are as defined in Formula I.

Compounds of Formula A wherein $R^1$, $R^2$ and $R^{4a-d}$ are as defined in Formula I may be prepared as shown in Scheme 2. Reagent F, in which R is, for example, benzyl, can be condensed with indole G, wherein $R^2$ and $R^{4a-d}$ are as defined in Formula I, typically by first converting the indole to a magnesium derivative by reaction with a suitable Grignard reagent, such as t-butyl- or ethyl-magnesium bromide, in an inert solvent. Then the magnesium derivative so formed can be reacted in situ with a reagent of Formula F to provide intermediates of Formula H. Suitable solvents include tetrahydrofuran and diethylether (which is preferred). The reaction can be conducted at temperatures ranging from $-30$ to $65°$ C., suitably at room temperature. Intermediate H may be reduced with hydride reducing agents to provide compounds of Formula A wherein $R^1$ is methyl. The preferred reducing conditions are lithium aluminum hydride in tetrahydrofuran at a temperature of around $65°$ C. Alternatively, intermediate H may be deprotected under standard conditions, for example sodium hydroxide in methanol, to provide intermediates of Formula J. Intermediate J may then be alkylated on the pyrrolidine nitrogen by treatment with a reagent of the formula $C_{2-4}$alkyl—X, wherein X is a suitable leaving group such as halogen, preferably bromo, in the presence of a mild base in an inert solvent to provide intermediates of Formula K. Suitable alkylation conditions include potassium carbonate in acetonitrile or triethylamine in dichloromethane. Temperatures may be in the range of 25 to $85°$ C., preferably at room temperature. Intermediates J and K may be reduced with hydride reducing agents as described above to provide compounds of Formula A, wherein $R^1$ is H and $C_{2-4}$alkyl respectively.

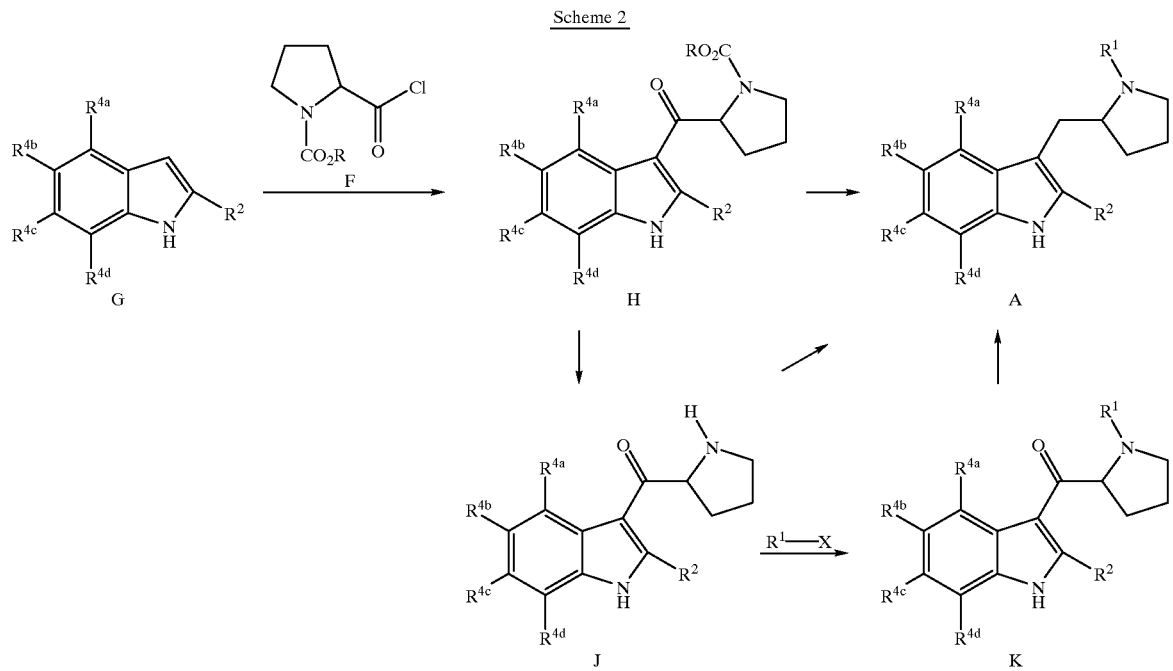

Scheme 2

Reagents of Formula A, wherein $R^1$ is a protecting group and $R^2$ and $R^{4a-d}$ are as defined in Formula I, are available by treating reagents of Formula A, wherein $R^1$ is H and $R^2$ and $R^{4a-d}$ are as defined in Formula I, under standard conditions to introduce a protecting group on the pyrrolidine nitrogen. For example, reaction of indole A, wherein $R^1$ is H, in the presence of di-t-butyldicarbonate and a base, such as sodium hydroxide, would provide compounds of Formula A wherein $R^1$ is the t-BOC protecting group.

The indoles of Formula G are either commercially available or can be prepared using standard procedures. For example, compounds of Formula G may be prepared as shown in Scheme 3. 4-Substituted anilines of Formula L, wherein $R^{4a-d}$ are as defined in Formula I, can be treated with reagents of Formula M, wherein $R^2$ is as defined in Formula I, in the presence of a base such as sodium bicarbonate or potassium carbonate in an alcoholic solvent at temperatures in the range of 60–100° C., to provide intermediates of Formula N. Preferred conditions are sodium bicarbonate in ethanol at around 80° C. Intermediates of Formula N can be cyclized in the presence of reagents of Formula O, wherein R is, for example, methyl or trifluoromethyl (which is preferred) at temperatures in the range of 60–100° C., to provide indoles of Formula P. The preferred conditions are trifluoroacetic anhydride and trifluoroacetic acid at refluxing temperatures. Finally, compounds of Formula P can be treated under standard deprotection conditions, for example alkali hydroxides in an alcoholic solvent, to provide indoles of Formula G, wherein $R^2$ and $R^{4a-d}$ are as defined in Formula I. Preferred conditions for this reaction are potassium hydroxide in ethanol at room temperature. The reagents of Formula L and M, are either commercially available or can be prepared using processes analogous to those established in the art.

procedure could also be used to prepare compounds of Formula G wherein $R^{4a}$, $R^{4c}$ or $R^{4d}$ are ethyl by reacting the appropriately substituted indole Q as described above.

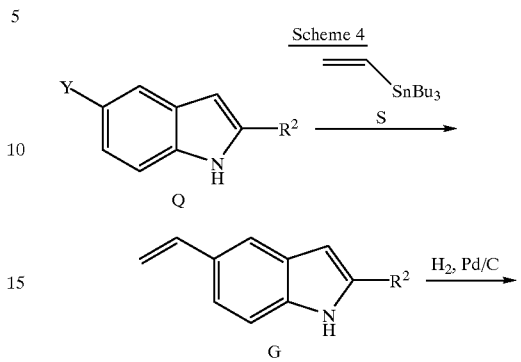

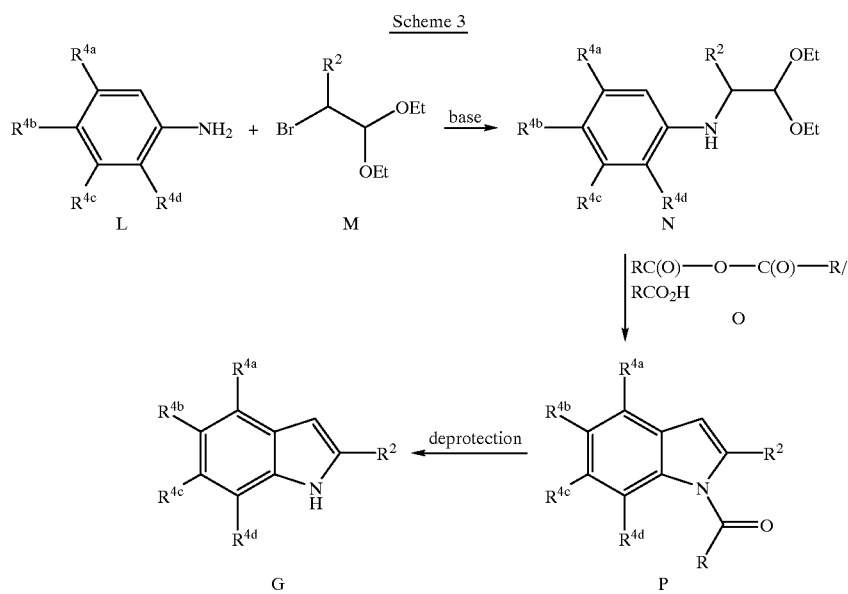

An alternative procedure for preparing indoles of Formula G wherein $R^{4b}$ is vinyl or ethyl is shown in Scheme 4. Indoles of Formula Q, wherein Y is a suitable leaving group such as halo or triflate (preferably bromo) and $R^2$ is as defined in Formula I, can be coupled with a vinyl trialkylstannane of, for example, Formula S, under standard palladium-cross coupling conditions to provide indoles of Formula G, wherein $R^{4c}$ is vinyl and $R^2$ is as defined in Formula I. It will be appreciated that other metal coupling reagents could be used in place of the vinyl stannane, for example, a vinyl boronic acid, chloro zinc and the like. Preferred coupling conditions include heating the indole and vinyl metal reagent in an inert solvent such as dimethylformamide or toluene in the presence of tetrakis (triphenylphosphine) palladium (0) at refluxing temperatures. Following the coupling reaction, the double bond of the vinyl group can be hydrogenated using catalytic amounts of palladium on carbon in an inert solvent (preferably ethyl acetate) in a hydrogen atmosphere at room temperature to provide indoles of Formula G wherein $R^{4c}$ is ethyl. This -continued

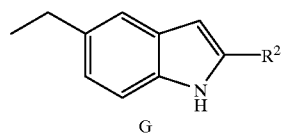

Indoles of Formula G, wherein $R^{4b}$ is cyclooxy or phenoxy and $R^2$ is as defined in Formula I, are also available from the corresponding 5-hydroxyindole T as shown in Scheme 5. Reaction of indole T with, for example, cyclohexanol U under standard Mitsunobu conditions (Mitsunobu, O. *Synthesis*, 1981:1–28) provides reagents of Formula G, wherein $R^{4b}$ is cyclohexyloxy and $R^2$ is as defined as Formula I. Reaction of indole T with reagent of Formula V wherein Y is an appropriate leaving group such as halo, preferably iodo, under standard Ulman conditions (Fanta, F. E., *Chem. Rev.*, 64, 1964:613) provides indoles of Formula G, wherein $R^{4b}$ is phenoxy and $R^2$ is as defined in Formula I. Preferred conditions are iodobenzene in the presence of potassium carbonate, copper (I) bromide and copper powder in N-methylpyrrolidine at 170° C.

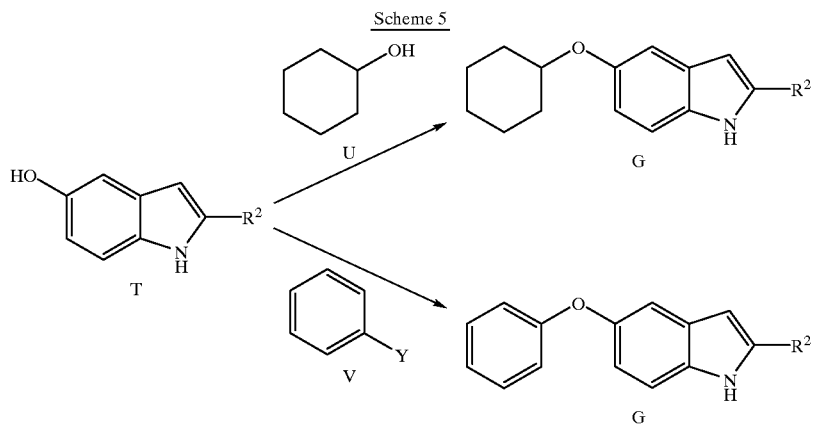

Scheme 5

The reactions shown in Schemes 4 and 5 could also be applied to indoles with the 3-(1-$R^1$-2-pyrrolidinylmethyl) group in place. In some cases, the chemistries outlined above may have to be modified, for instance by use of protecting groups, to prevent side reactions due to reactive groups, such as reactive groups attached as substituents.

In another embodiment of the invention, the present compounds can be used to distinguish 5-$HT_6$ receptors from other receptor subtypes, for example glutamate or opioid receptors, within a population of receptors, and in particular to distinguish between the 5-$HT_6$ and other 5-HT receptor subtypes. The latter can be achieved by incubating preparations of the 5-$HT_6$ receptor and one of the other 5-HT receptor subtypes (for example 5-HT2A) with a 5-$HT_6$-selective compound of the invention and then incubating the resulting preparation with a radiolabeled serotonin receptor ligand, for example [$^3$H]-serotonin. The 5-$HT_6$ receptors are then distinguished by determining the difference in membrane-bound activity, with the 5-$HT_6$ receptor exhibiting lesser radioactivity, i.e., lesser [$^3$H]-serotonin binding, than the other 5-HT receptor subtype.

In another embodiment of the invention, the compound is provided in labeled form, such as radiolabeled form, e. g. labeled by incorporation within its structure $^3$H or $^{14}$C or by conjugation to $^{125}$I. In another aspect of the invention, the compounds in labeled form can be used to identify 5-$HT_6$ receptor ligands by techniques common in the art. This can be achieved by incubating the receptor or tissue in the presence of a ligand candidate and then incubating the resulting preparation with an equimolar amount of radiolabeled compound of the invention such as [$^3$H]-5-chloro-1-(4-fluorobenzoyl)-3-(1-methyl-2-pyrrolidinylmethyl)indole. 5-$HT_6$ receptor ligands are thus revealed as those that are not significantly displaced by the radiolabeled compound of the present invention. Alternatively, 5-$HT_6$ receptor ligand candidates may be identified by first incubating a radiolabeled form of a compound of the invention then incubating the resulting preparation in the presence of the candidate ligand. A more potent 5-$HT_6$ receptor ligand will, at equimolar concentration, displace the radiolabeled compound of the invention.

The present compounds are useful as pharmaceuticals for the treatment of various conditions in which the use of a 5-$HT_6$ antagonist is indicated, such as psychosis, schizophrenia, manic depression, depression, neurological disturbances, memory disturbances, Parkinsonism, amyotrophic lateral sclerosis, Alzheimer's disease and Huntington's disease. In another of its aspects, the present invention provides pharmaceutical compositions useful to treat 5-$HT_6$-related medical conditions, in which a compound of Formula I is present in an amount effective to antagonize 5-$HT_6$ receptor stimulation, together with a pharmaceutically acceptable carrier. In a related aspect, the invention provides a method for treating medical conditions for which a 5-$HT_6$ receptor antagonist is indicated, which comprises the step of administering to the patient an amount of a compound of Formula I effective to antagonize 5-$HT_6$ receptor stimulation, an a pharmaceutically acceptable carrier therefor.

For use in medicine, the compounds of the present invention can be administered in a standard pharmaceutical composition. The present invention therefore provides, in a further aspect, pharmaceutical compositions comprising a pharmaceutically acceptable carrier and a Formula I compound or a pharmaceutically acceptable salt, solvate or hydrate thereof, in an amount effective to treat the target indication.

The compounds of the present invention may be administered by any convenient route, for example by oral, parenteral, buccal, sublingual, nasal, rectal, patch, pump or transdermal administration and the pharmaceutical compositions formulated accordingly.

Compounds of Formula I and their pharmaceutically acceptable salts which are active when given orally can be formulated as liquids, for example syrups, suspensions or emulsions, or as solid forms such as tablets, capsules and lozenges. A liquid formulation will generally consist of a suspension or solution of the compound or pharmaceutically acceptable salt in a suitable pharmaceutical liquid carrier for example, ethanol, glycerine, non-aqueous solvent, for example polyethylene glycol, oils, or water with a suspending agent, preservative, flavouring or colouring agent. A composition in the form of a tablet can be prepared using any suitable pharmaceutical carrier routinely used for preparing solid formulations. Examples of such carriers include magnesium stearate, starch, lactose, sucrose and cellulose. A composition in the form of a capsule can be prepared using routine encapsulation procedures. For example, pellets containing the active ingredient can be prepared using standard carriers and then filled into hard gelatin capsule; alternatively, a dispersion or suspension can be prepared using any suitable pharmaceutical carrier, for example aqueous gums, celluloses, silicates or oils and the dispersion or suspension filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, arachis oil or sesame oil. Alternatively, the solution can be lyophilized and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Preferably, the composition is in unit dose form such as a tablet, capsule or ampoule. Suitable unit dosages, i.e. therapeutically effective amounts, can be determined during clinical trials designed appropriately for each of the conditions for which administration of a chosen compound is indicated and will of course vary depending on the desired clinical endpoint. Each dosage unit for oral administration may contain from 0.01 to 500 mg/kg (and for parenteral administration may contain from 0.1 to 50 mg) of a compound of Formula I, or a pharmaceutically acceptable salt thereof calculated as the free base, and will be administered in a frequency appropriate for initial and maintenance treatments. For laboratory use, the present compounds can be stored in packaged form for reconstitution and use.

EXPERIMENTAL EXAMPLES

Example 1
5-Cyclohexyloxy-1H-indole:

Triphenylphosphine (10.3 g, 39.4 mmol) and 5-hydroxyindole (5 g, 36.9 mmol) were added to a solution of cyclohexanol (3.7 mL, 35.7 mmol) in THF (200 mL) at 0° C. DEAD (5.9 mL, 39.4 mmol) was slowly added and the resulting solution was stirred for I week at room temperature. The solvent was removed in vacuo and flash chromatography (silica gel, 10% ethyl acetate in hexane) yielded 5-cyclohexyloxyindole (3.2 g, 40%).

Example 2(a)
(R)-3-[(N-Benzyloxycarbonylpyrrolidin-2-yl)carbonyl]-5-bromo-1H-indole To a stirred solution of N-benzyloxycarbonyl-R-proline (2.5 g, 10.0 mmol) in anhydrous methylene chloride was added a solution of oxalyl chloride (2M solution in methylene chloride, 7 mL, 15.0 mmol). The resulting mixture was stirred at room temperature under argon for 2 hours. The solvent and excess oxalyl chloride were evaporated under reduced pressure and the crude product washed with hexane (3×10 mL) and evaporated to dryness to provide N-benzyloxycarbonyl-R-proline acid chloride which was used directly for the next reaction.

N-Benzyloxycarbonyl-R-proline acid chloride from the above reaction was dissolved in anhydrous diethyl ether (30 mL) and added at 0° C. to a solution of 5-bromoindole (2.9 g, 15.0 mmol) and t-butylmagnesium chloride (2M solution in diethyl ether, 8.3 mL, 16.5 mmol) in anhydrous diethyl ether (30 mL). The resulting mixture was stirred at room temperature under argon for 45 minutes and then ethyl acetate (150 mL) and saturated sodium bicarbonate (30 mL) were added. The organic layer was dried and evaporated under reduced pressure to provide a yellow oil. The title compound was crystallized using hexane/ethyl acetate (9:1) to provide a white solid (3.07 g, 72%). mp 95–96° C.

In a like manner, the following additional compounds were prepared:

(b) (R)-3-[(N-Benzyloxycarbonylpyrrolidin-2-yl) carbonyl]-5-methyl-1H-indole: from 5-methyl-1H-indole;

(c) (R)-3-[(N-Benzyloxycarbonylpyrrolidin-2-yl) carbonyl]-5-chloro-1H-indole: from 5-chloro-1H-indole;

(d) (R)-3-[(N-Benzyloxycarbonylpyrrolidin-2-yl) carbonyl]-5-fluoro-1H-indole: from 5-fluoro-1H-indole;

(e) (R)-3-[(N-Benzyloxycarbonylpyrrolidin-2-yl) carbonyl]-1H-indole: from 1H-indole;

(f) (R)-3-[(N-Benzyloxycarbonylpyrrolidin-2-yl) carbonyl]-5-benzyloxy-1H-indole: from 5-benzyloxy-1H-indole; and (g) (R)-3-[(N-Benzyloxycarbonylpyrrolidin-2-yl) carbonyl]-5-cyclohexyloxy-1H-indole: from 5-cyclohexyloxy-1H-indole (Example 1).

Example 3(a)
(R)-5-Methyl-3-(1-methyl-2-pyrrolidinylmethyl)-1H-indole

A solution of LAH (39 mL, 1 M in THF, 39 mmol) was added slowly to a cooled (0° C.) solution of (R)-3-[(N-benzyloxycarbonylpyrrolidin-2-yl)carbonyl]-5-methyl-1H-indole (Example 1b, 9.5 mmol) in THF (100 mL). Once the addition was completed, the reaction mixture was stirred at reflux overnight prior to quenching with sodium sulfate decahydrate. The product was taken into ethyl acetate, filtered to remove the solid residue, and the solvent was removed in vacuo. The product was taken into ethyl acetate, filtered to remove the solid residue, and the solvent was removed in vacuo. Flash chromatography (silica gel, 6% 2M methanolic ammonia in dichloromethane) yielded (R)-5-methyl-3-(1-methyl-2-pyrrolidinylmethyl)-1H-indole (52%; yellow oil; HRMS-FAB$^+$ for $C_{15}H_{20}N_2$: calculated MH$^+$:229.1705; found MH$^+$:229.1706).

In a like manner, the following additional compounds were prepared:

(b) (R)-5-Bromo-3-(1-methyl-2-pyrrolidinylmethyl)-1H-indole: from (R)-3-[(N-benzyloxycarbonylpyrrolidin-2-yl)carbonyl]-5-bromo-1H-indole (Example 2a);

(c) (R)-5-Chloro-3-(1-methyl-2-pyrrolidinylmethyl)-1H-indole: from (R)-3-[(N-benzyloxycarbonylpyrrolidin-2-yl)carbonyl]-5-chloro-1H-indole (Example 2c);

(d) (R)-5-Fluoro-3-(1-methyl-2-pyrrolidinylmethyl)-1H-indole: from (R)-3-[(N-benzyloxycarbonylpyrrolidin-2-yl)carbonyl]-5-fluoro-1H-indole (Example 2b);

(e) (R)-3-(1-Methyl-2-pyrrolidinylmethyl)-1H-indole: from (R)-3-[(N-benzyloxycarbonylpyrrolidin-2-yl) carbonyl]-1H-indole (Example 2e);

(f) (R)-5-Benzyloxy-3-(1-methyl-2-pyrrolidinylmethyl)-1H-indole: from (R)-3-[(N- benzyloxycarbonylpyrrolidin-2-yl)carbonyl]-5-benzyloxy-1H-indole (Example 2f); and (g) (R)-5-Cyclohexyloxy-3-(1-methyl-2-pyrrolidinylmethyl)-1H-indole: from (R)-3-[(N-benzyloxycarbonylpyrrolidin-2-yl)carbonyl]-5-cyclohexyloxy-1H-indole (Example 2g).

Example 4

(R)-5-Cyclohexyloxy-3-(1-methyl-2-pyrrolidinylmethyl)-1-phenylsulfonylindole n-Butyllithium (0.19 mL, 1.45M in hexane, 0.28 mmol) was added to a solution of (R)-5-cyclohexyloxy-3-(1-methyl-2-pyrrolidinylmethyl)-1H-indole (Example 3g, 77.1 mg, 0.25 mmol) in THF (1 mL) at −78° C.; the temperature was raised to 0 ° C. and the mixture was stirred for 40 min. After recooling to −78° C., phenylsulfonyl chloride (60 μL, 0.47 mmol) was added and the mixture was allowed to warm to room temperature slowly (overnight). The mixture was quenched with water (5 mL) and extracted into dichloromethane. The organic layer was washed sequentially with water and brine, and dried over sodium sulfate. Purification by flash chromatography (silica gel, 1–4% 2M methanolic ammonia in chloroform) yielded (R)-5-cyclohexyloxy-3-(1-methyl-2-pyrrolidinylmethyl)-1-phenylsulfonylindole (19.1 mg, 17%, HRMS-FAB$^+$ for $C_{26}H_{32}N_2O_3S$: calculated MH$^+$:453.22119; found MH$^+$:453.22550).

Example 5(a)

(R)-3-(1-Methyl-2-pyrrolidinylmethyl)-1-phenylsulfonylindole

Sodium bis(trimethylsilyl)amide (0.25 mL, 1M in THF, 0.25 mmol) was added to a solution of (R)-3-(1-methyl-2-pyrrolidinylmethyl)-1H-indole (Example 3e, 25.8 mg, 0.12 mmol) in THF (1.5 mL) at −78° C. and the mixture was stirred for 1 h. Phenylsulfonyl chloride (50 μL, 0.39 mmol) was added and the mixture stirred at room temperature for 1 h. prior to quenching with water (6 drops) and silica gel (~1 g). Purification using solid phase extraction tubes (1000 mg silica) eluting with 2M methanolic ammonia in dichloromethane (0–4%) yielded (R)-3-(1-methyl-2-pyrrolidinylmethyl)-1-phenylsulfonylindole (19.7 mg, 46%, HRMS-FAB$^+$ for $C_{20}H_{22}N_2O_2S$: calculated MH$^+$:355.14801; found MH$^+$:355.14837).

In a like manner, the following additional compounds were prepared:

(b) (R)-1-(4-Methoxyphenylsulfonyl)-3-(1-methyl-2-pyrrolidinylmethyl)indole: (28.1 mg, 61 %); from (R)-3-(1-methyl-2-pyrrolidinylmethyl)-1H-indole (Example 3e, 25.8 mg, 0.12 mmol) and 4-methoxyphenylsulfonyl chloride (50 mg, 0.24 mmol); HRMS-FAB$^+$ for $C_{21}H_{24}N_2O_3S$: calculated MH$^+$:385.15860; found MH$^+$:385.15891.

(c) (R)-1-(4-Fluorophenylsulfonyl)-3-(1-methyl-2-pyrrolidinylmethyl)indole: (27.2 mg, 61 %); from (R)-3-(1-methyl-2-pyrrolidinylmethyl)-1H-indole (Example 3e, 25.8 mg, 0.12 mmol) and 4-fluorophenylsulfonyl chloride (50 mg, 0.26 mmol); HRMS-FAB$^+$ for $C_{20}H_{21}N_2O_2SF$: calculated MH$^+$:373.13861; found MH$^+$:373.13872.

(d) (R)-5-Chloro-3-(1-methyl-2-pyrrolidinylmethyl)-1-phenylsulfonylindole: (18.1 mg, 46% yield); from (R)-5-chloro-3-(1-methyl-2-pyrrolidinylmethyl)-1H-indole (Example 3c, 25.8 mg, 0.103 mmol) and phenylsulfonyl chloride (36.3 mg, 0.206 mmol), HRMS-FAB$^+$: $C_{20}H_{21}N_2O_2SCl$, calculated MH$^+$:389.10904; found MH$^+$:389.10749.

(e) (R)-5-Chloro-1-(4-methoxyphenylsulfonyl)-3-(1-methyl-2-pyrrolidinylmethyl)indole: (16.5 mg, 40% yield); from (R)-5-chloro-3-(1-methyl-2-pyrrolidinylmethyl)-1H-indole (Example 3c, 25.9 mg, 0.103 mmol) and 4-methoxyphenylsulfonyl chloride (42.4 mg, 0.206 mmol), HRMS-FAB$^+$: $C_{21}H_{23}N_2O_3SCl$, calculated MH$^+$:419.11963; found MH$^+$:419.11552.

(f) (R)-5-Chloro-1-(4-fluorophenylsulfonyl)-3-(1-methyl-2-pyrrolidinylmethyl)indole: (21.1 mg, 52% yield); from (R)-5-chloro-3-(1-methyl-2-pyrrolidinylmethyl)-1H-indole (Example 3c, 26.8 mg, 0.107 mmol) and 4-fluorophenylsulfonyl chloride (41.5 mg, 0.214 mmol), HRMS-FAB$^+$: $C_{20}H_{20}N_2O_2SClF$, calculated MH$^+$:407.09964; found MH$^+$:407.10291.

(g) (R)-1-Benzoyl-3-(1-methyl-2-pyrrolidinylmethyl) indole: (21.4 mg, 56%); from (R)-3-(1-methyl-2-pyrrolidinylmethyl)-1H-indole (Example 3e, 26.0 mg, 0.12 mmol) and benzoyl chloride (50 μL, 0.43 mmol); HRMS-FAB$^+$ for $C_{21}H_{22}N_2O$: calculated MH$^+$:319.18103; found MH$^+$:319.17955.

(h) (R)-1-(4-Methoxybenzoyl)-3-(1-methyl-2-pyrrolidinylmethyl)indole: (30 mg, 72%); from (R)-3-(1-methyl-2-pyrrolidinylmethyl)-1H-indole (Example 3e, 26 mg, 0.12 mmol) and 4-methoxybenzoyl chloride (50 μL, 0.34 mmol); HRMS-FAB$^+$ for $C_{22}H_{24}N_2O_2$: calculated MH$^+$:349.19159; found MH$^+$:349.19034.

(i) (R)-1-(4-Fluorobenzoyl)-3-(1-methyl-2-pyrrolidinylmethyl)indole: (34.8 mg, 86%); from (R)-3-(1-methyl-2-pyrrolidinylmethyl)-1H-indole (Example 3e, 25.9 mg, 0.12 mmol) and 4-fluorobenzoyl chloride (50 μL, 0.42 mmol); HRMS-FAB$^+$ for $C_{21}H_{21}N_2OF$: calculated MH$^+$:337.17163; found MH$^+$:337.17138.

(j) (R)-1-(2-Chlorobenzoyl)-5-cyclohexyloxy-3-(1-methyl-2-pyrrolidinylmethyl)indole: (18.6 mg, 56%); from (R)-5-cyclohexyloxy-3-(1-methyl-2-pyrrolidinylmethyl)-1H-indole (Example 3g, 22.8 mg, 0.073 mmol) and 2-chlorobenzoyl chloride (19.5 μL, 0.15 mmol); HRMS-FAB$^+$ for $C_{27}H_{31}N_2O_2Cl$: calculated MH$^+$:451.21524; found MH$^+$:451.21488.

(k) (R)-5-Cyclohexyloxy-1-(2-methoxybenzoyl)-3-(1-methyl-2-pyrrolidinylmethyl)indole: (15.4 mg, 44%); from (R)-5-cyclohexyloxy-3-(1-methyl-2-pyrrolidinylmethyl)-1H-indole (Example 3g, 24.6 mg, 0.079 mmol) and 2-methoxybenzoyl chloride (24 μL, 0.16 mmol); HRMS-FAB$^+$ for $C_{28}H_{34}N_2O_3$: calculated MH$^+$:447.26477; found MH$^+$:447.26434.

(l) (R)-5-Cyclohexyloxy-1-(4-methoxybenzoyl)-3-(1-methyl-2-pyrrolidinylmethyl)indole: (24.3 mg, 69%); from (R)-5-cyclohexyloxy-3-(1-methyl-2-pyrrolidinylmethyl)-1H-indole (Example 3g, 24.7 mg, 0.079 mmol) and 4-methoxybenzoyl chloride (24 μL, 0.16 mmol); HRMS-FAB$^+$ for $C_{28}H_{34}N_2O_3$: calculated MH$^+$:447.26477; found MH$^+$:447.26630.

(m) (R)-5-Cyclohexyloxy-1-(3,4-methylenedioxybenzoyl)-3-(1-methyl-2-pyrrolidinylmethyl)indole: (24.8 mg, 68%); from (R)-5-cyclohexyloxy-3-(1-methyl-2-pyrrolidinylmethyl)-1H-indole (Example 3g, 24.7 mg, 0.079 mmol) and 3,4-methylenedioxybenzoyl chloride (31 mg, 0.17 mmol); HRMS-FAB$^+$ for $C_{28}H_{32}N_2O_4$: calculated MH$^+$:461.24402; found MH$^+$:461.24525.

(n) (R)-5-Cyclohexyloxy-1-(2,6-dichlorobenzoyl)-3-(1-methyl-2-pyrrolidinylmethyl)indole: (28.7 mg, 75%); from (R)-5-cyclohexyloxy-3-(1-methyl-2-pyrrolidinylmethyl)-1H-indole (Example 3g, 24.7 mg, 0.079 mmol) and 2,6-dichlorobenzoyl chloride (23 μL, 0.16 mmol.

(o) (R)-5-Cyclohexyloxy-3-(1-methyl-2-pyrrolidinylmethyl)-1-(2-thienoyl)indole: (15.4 mg, 46%); from (R)-5-cyclohexyloxy-3-(1-methyl-2-pyrrolidinylmethyl)-1H-indole (Example 3g, 24.8 mg, 0.079 mmol) and 2-thiophenecarbonyl chloride (17 μL, 0.16 mmol); HRMS-FAB+ for $C_{25}H_{30}N_2O_2S$: calculated MH+:423.21063; found MH+:423.20947.

(p) (R)-1-Benzoyl-5-chloro-3-(1-methyl-2-pyrrolidinylmethyl)indole: (28 mg, 66% yield); from (R)-5-chloro-3-(1-methyl-2-pyrrolidinylmethyl)-1H-indole (Example 3c, 30 mg, 0.12 mmol) and benzoyl chloride (33.7 mg, 0.24 mmol), HRMS-FAB+: $C_{21}H_{21}N_2OCl$, calculated MH+:353.14206; found MH+: 353.14528.

(q) (R)-5-Chloro-1-(4-methoxybenzoyl)-3-(1-methyl-2-pyrrolidinylmethyl)indole: (24 mg, 52% yield); from (R)-5-chloro-3-(1-methyl-2-pyrrolidinylmethyl)-1H-indole (Example 3c, 30 mg, 0.12 mmol) and 4-methoxybenzoyl chloride (40.9 mg, 0.24 mmol), HRMS-FAB+: $C_{22}H_{23}ClN_2O_2$, calculated MH+:383.15262; found MH+:383.14917.

(r) (R)-5-Chloro-1-(4-fluorobenzoyl)-3-(1-methyl-2-pyrrolidinylmethyl)indole: (6.8 mg, 15% yield); from (R)-5-chloro-3-(1-methyl-2-pyrrolidinylmethyl)-1H-indole (Example 3c, 30 mg, 0.12 mmol) and 4-fluorobenzoyl chloride (38.1 mg, 0.24 mmol), HRMS-FAB+: $C_{21}H_{20}N_2OClF$, calculated MH+:371.13263; found MH+:371.13285.

Example 6(a)
(R)-5-Cyclohexyloxy-3-(1-methyl-2-pyrrolidinylmethyl)-1-(S-methylxanthyl)indole Sodium bis(trimethylsilyl)amide (0.49 mL, 1M in THF, 0.49 mmol) was added to a solution of (R)-5-cyclohexyloxy-3-(1-methyl-2-pyrrolidinylmethyl)-1H-indole (Example 3g, 76.3 mg, 0.24 mmol) in THF (2.5 mL) at –78° C. and the mixture was stirred for 1 h. Carbon disulfide (30 μL, 0.50 mmol) was added and the mixture stirred at room temperature for 1 h. at –78° C. prior to quenching with methyl iodide (30 μL, 0.48 mmol). The mixture was allowed to warm to room temperature slowly (overnight). Purification by flash chromatography (silica gel, 2M methanolic ammonia in dichloromethane (2–4%) yielded (R)-5-cyclohexyloxy-3-(1-methyl-2-pyrrolidinylmethyl)-1-(S-methylxanthyl)indole (42.7 mg, 43%, HRMS-FAB+ for $C_{22}H_{30}N_2OS_2$: calculated MH+:403.18777; found MH+:403.18795).

In a like manner, the following additional compounds were prepared:

(b) (R)-5-Cyclohexyloxy-3-(1-methyl-2-pyrrolidinylmethyl)-1-[S-(4-cyanobenzyl)xanthyl]indole: (14.5 mg, 18%); from (R)-5-cyclohexyloxy-3-(1-methyl-2-pyrrolidinylmethyl)-1H-indole (Example 3g, 50 mg, 0.16 mmol), carbon disulfide (25 μL, 0.41 mmol) and 4-cyanobenzyl bromide (64 mg, 0.33 mmol); HRMS-FAB+ for $C_{29}H_{33}N_3OS_2$: calculated MH+:504.21432; found MH+:504.21887.

(c) (R)-5-Cyclohexyloxy-3-(1-methyl-2-pyrrolidinylmethyl)-1-(S-benzylxanthyl)indole: (10.7 mg, 13%); from (R)-5-cyclohexyloxy-3-(1-methyl-2-pyrrolidinylmethyl)-1H-indole (Example 3g, 51.9 mg, 0.17 mmol), carbon disulfide (25 μL, 0.41 mmol) and benzyl bromide (56 μL, 0.47 mmol); HRMS-FAB+ for $C_{28}H_{34}N_2OS_2$: calculated MH+:479.21909; found MH+:479.21784.

(d) (R)-5-Methyl-3-(1-methyl-2-pyrrolidinylmethyl)-1-(S-methylxanthyl)indole: (21.0 mg, 36%); from (R)-5-methyl-3-(1-methyl-2-pyrrolidinylmethyl)-1H-indole (Example 3a, 41.3 mg, 0.181 mmol), carbon disulfide (28 mg, 0.362 mmol) and methyl iodide (0.362 mmol); HRMS-FAB+ for $C_{17}H_{23}N_2S_2$ calculated MH+: 319.13028; found MH+:319.13390.

(e) (R)-5-Fluoro-3-(1-methyl-2-pyrrolidinylmethyl)-1-(S-methylxanthyl)indole: (0.055 g, 66%) from (R)-5-fluoro-3-(1-methyl-2-pyrrolidinylmethyl)-1H-indole (Example 3d, 0.060 g, 0.258 mmol) and carbon disulfide (39 Mg, 0.516 mmol) and methyl iodide (73 Mg, 0.516 mmol); HRMS-FAB+ for $C_{16}H_{20}N_2S_2F$ calculated MH+:323.10519; found MH+:323.10585.

(f) (R)-1-(S-Benzylxanthyl)-5-fluoro-(1-methyl-2-pyrrolidinylmethyl)indole: (19.3 mg, 53%) from (R)-5-fluoro-3-(1-methyl-2-pyrrolidinylmethyl)-1H-indole (Example 3d, 20.9 mg, 0.092 mmol) and carbon disulfide (14.1 mg, 0.184 mmol) and benzyl bromide (31.4 mg, 0.184 mmol); HRMS-FAB+ for $C_{22}H_{24}N_2S_2F$ calculated MH+:399.13651; found MH+:399.13687.

(g) (R)-1-(S-Allylxanthyl)-5-fluoro-3-(1-methyl-2-pyrrolidinylmethyl)indole: (22.8 mg, 65%) from (R)-5-fluoro-3-(1-methyl-2-pyrrolidinylmethyl)-1H-indole (Example 3d, 23.0 mg, 0.101 mmol), carbon disulfide (15.3 mg, 0.202 mmol) and allyl bromide (24.5 mg, 0.202 mmol); HRMS-FAB+ for $C_{18}H_{22}N_2S_2F$ calculated MH+:349.12085; found MH+:349.12188.

(h) (R)-5-Fluoro-3-(1-methyl-2-pyrrolidinylmethyl)-1-(S-propargylxanthyl)indole: (19.0 mg, 50%) from (R)-5-fluoro-3-(1-methyl-2-pyrrolidinylmethyl)-1H-indole (Example 3d, 24.9 mg, 0.109 mmol), carbon disulfide (16.6 mg, 0.218 mmol) and propargyl bromide (25.9 mg, 0.218 mmol); HRMS-FAB+ for $C_{18}H_{20}N_2S_2F$ calculated MH+:347.10519; found MH+: 347.10180.

(i) (R)-3-(1-Methyl-2-pyrrolidinylmethyl)-1-(S-methylxanthyl)indole: (32 mg, 39%) from (R)-3-(1-methyl-2-pyrrolidinylmethyl)-1H-indole (Example 3e, 58 mg, 0.273 mmol), carbon disulfide (41 mg, 0.546 mmol) and methyl iodide (77 mg, 0.546 mmol); HRMS-FAB+ for $C_{16}H_{21}N_2S_2$ calculated MH+: 305.11462, found MH+:305.11289.

(j) (R)-1-(S-Benzylxanthyl)-3-(1-methyl-2-pyrrolidinylmethyl)indole: (17.3 mg, 36%) from (R)-3-(1-methyl-2-pyrrolidinylmethyl)-1H-indole (Example 3e, 27.0 mg, 0.126 mmol), carbon disulfide (19.1 mg, 0.252 mmol) and benzyl bromide (43.1 mg, 0.252 mmol); HRMS-FAB+ for $C_{22}H_{25}N_2S_2$ calculated MH+: 381.14590; found MH+:381.14467.

(k) (R)-1-(S-Allylxanthyl)-3-(1-methyl-2-pyrrolidinylmethyl)indole: (19.2 mg, 50%) from (R)-3-(1-methyl-2-pyrrolidinylmethyl)1H-indole (Example 3e, 24.9 mg, 0.116 mmol) and carbon disulfide (17.7 mg, 0.232 mmol) and allyl bromide (28.0 mg, 0.232 mmol); HRMS-FAB+ for $C_{18}H_{23}N_2S_2$ calculated MH+: 331.13028; found MH+:331.13324.

Example 7(a)
(R)-5-Cyclohexyloxy-3-(1-methyl-2-pyrrolidinylmethyl)-1-benzoylindole Benzoyl chloride (0.10 mL, 0.86 mmol) was added to a solution of (R)-5-cyclohexyloxy-3-(1-methyl-2-pyrrolidinylmethyl)-1H-indole (Example 3g, ~75 mg, 0.24 mmol), triethylamine (0.20 mL, 1.4 mmol) and DMAP (23 mg, 0.19 mmol) in dichloromethane (2.5 mL). The mixture was stirred for 15 h. prior to quenching with water (25 mL) and extraction into dichloromethane. The organic layer was washed with brine and dried over sodium sulfate. Purification by flash chromatography (silica gel, 2M methanolic ammonia in chloroform (1.5–3.3%) yielded (R)-5-cyclohexyloxy-3-(1-methyl-2-pyrrolidinylmethyl)-1-benzoylindole (20.1 mg, 20%, HRMS-FAB+ for $C_{27}H_{32}N_2O_2$: calculated MH+:417.25421; found MH+:417.25475).

In a like manner, the following additional compounds were prepared:

(b) (R)-5-Cyclohexyloxy-3-(1-methyl-2-pyrrolidinylmethyl)-1-(4-methylphenylsulfonyl)indole: (9.2 mg, 11%); from (R)-5-cyclohexyloxy-3-(1-methyl-2-pyrrolidinylmethyl)-1H-indole (Example 3g, 54.2 mg, 0.17 mmol) and 4-methylphenylsulfonyl chloride (41.2 mg, 0.22 mmol); HRMS-FAB$^+$ for $C_{27}H_{34}N_2O_3S$: calculated MH$^+$:467.23685; found MH$^+$:467.24074;

(c) (R)-5-Fluoro-1-(4-methylphenylsulphonyl)-3-(1-methyl-2-pyrrolidinylmethyl)-indole: (11.5 mg, 17%) from (R)-5-fluoro-3-(1-methyl-2-pyrrolidinylmethyl)-1H-indole (Example 3d, 40.2 mg, 0.17 mmol) and 4-methylphenylsulphonyl chloride (36.2 mg, 0.19 mmol); HRMS-FAB$^+$ for $C_{21}H_{24}N_2O_2SF$ calculated MH$^+$:387.15427; found MH$^+$:387.15548;

(d) (R)-1-Benzoyl-5-bromo-3-(1-methyl-2-pyrrolidinylmethyl) indole: (198 mg, 50%) from (R)-5-bromo-3-(1-methyl-2-pyrrolidinylmethyl)-1H-indole (Example 3b, 90 mg, 0.99 mmol) and benzoyl chloride (0.15 g, 1.09 mmol); HRMS-FAB$^+$ for $C_{21}H_{22}N_2OBr$ calculated MH$^+$:397.09155; found MH$^+$:397.09155.

e) (R)-5-Benzyloxyindole-3-(1-methyl-2-pyrrolidinylmethyl)-1-phenylsulfonylindole: from 5-benzyloxyindole-3-(1-methyl-2-pyrrolidinylmethyl)indole (Example 3f, 200 mg, 0.62 mmol) and phenylsulfonyl chloride (95.5 uL, 0.75 mmol.

Example 8

(R)-5-Benzyloxy-3-(1-methyl-2-pyrrolidinylmethyl)-1-(N-methylcarboxamido)indole

N-Methyl isocyanate (18.7 μL, 0.32 mmol) was added to a solution of (R)-5-benzyloxy-3-(1-methyl-2-pyrrolidinylmethyl)-1H-indole (Example 3f, 75 mg, 0.23 mmol) and triethylamine (0.17 mL, 1.2 mmol) in toluene (3 mL) and the mixture was stirred at reflux until disappearance of the starting indole was indicated by tlc. The cooled reaction mixture was diluted with dichloromethane and washed sequentially with water and brine. Flash chromatography (silica gel, 7% 2M methanolic ammonia in dichloromethane) yielded (R)-5-benzyloxy-3-(1-methyl-2-pyrrolidinylmethyl)-1-(N-methylcarboxamido)indole (48.2 mg, 54%).

Example 9

(R)-5-Hydroxy-3-(1-methyl-2-pyrrolidinylmethyl)-1-(N-methylcarboxamido)indole

Palladium on carbon (10%, 20 mg) was added to a solution of (R)-5-benzyloxy-3-(1-methyl-2-pyrrolidinylmethyl)-1-(N-methylcarboxamido)-1H-indole (Example 8, 40 mg, 0.105 mmol) in ethyl acetate (1 mL) and methanol (1 mL) and the mixture was stirred under an atmosphere of hydrogen until disappearance of the starting indole was indicated by tlc. Removal of the catalyst by filtration followed by flash chromatography (silica gel, 10% 2M methanolic ammonia in dichloromethane) yielded (R)-5-hydroxy-3-(1-methyl-2-pyrrolidinylmethyl)-1-(N-methylcarboxamido)indole.

Example 10

(R)-1-Phenylsulfonyl-5-hydroxy-3-(1-methyl-2-pyrrolidinylmethyl)indole

A solution of (R)-5-benzyloxy-3-(1-methyl-2-pyrrolidinylmethyl)-1-phenylsulfonylindole (Example 7e, 2.01 g, 4.36 mmol) and 10% Pd/C (0.64 g, 0.436 mmol) in ethanol (25 mL) was stirred under an atmosphere of H$_2$. Filtration to remove the catalyst followed by flash chromatography (silica gel) yielded (R)-5-hydroxy-3-(1-methyl-2-pyrrolidinylmethyl)-1-phenylsulfonylindole (1.5 g, 93%; HRMS-FAB$^+$: $C_{20}H_{22}N_2O_3S$, calculated MH$^+$:371.14294; found MH$^+$:371.14081).

Example 11

(R)-1-Phenylsulfonyl-5-phenoxy-3-(1-methyl-2-pyrrolidinylmethyl)indole

A solution of (R)-5-hydroxy-3-(1-methyl-2-pyrrolidinylmethyl)-1-phenylsulfonylindole (Example 10, 74 mg, 0.20 mmol) and iodobenzene (61.2 mg, 0.3 mmol) with $K_2CO_3$ (41.4 mg 0.30 mmol), CuBr (17.2 0.12 mmol) and Cu powder (10 mg, 0.15 mmol) in NMP (0.7 mL) was heated at 170° C. Aqueous workup and flash chromatography (silica gel) yielded (R)-3-(1-methyl-2-pyrrolidinylmethyl)5-phenoxy-1-phenylsulfonylindole (5.8 mg, 8%, HRMS-FAB$^+$: $C_{26}H_{26}N_2O_3S$, calculated MH$^+$:447.17422; found MH$^+$: 447.17240).

Example 12(a)

(R)-2-Benzyl-5-hydroxy-3-(1-methyl-2-pyrrolidinylmethyl)-1-phenylsulfonylindole n-Butyllithium (0.10 mL, 1.45M in hexane, 0.14 mmol) was added to a solution of (R)-5-benzyloxy-3-(1-methyl-2-pyrrolidinylmethyl)-1-phenylsulfonylindole (Example 7e, 24 mg, 0.052 mmol) in THF (2 mL) at −78° C.; the temperature was raised to 0° C. and the mixture was stirred for 20 min. After recooling to −78° C., benzyl bromide (18 μL, 0.15 mmol) was added and the mixture was stirred for 1 h at 78° C.; then 15 min. without cooling prior to quenching with water and extraction with ethyl acetate. The organic layer was washed sequentially with water and brine, and dried over sodium sulfate. Palladium on carbon (10%) was added to a solution of the crude product in methanol (2 mL) and the mixture was stirred under an atmosphere of hydrogen for 1.5 h. Removal of the catalyst by filtration followed by flash chromatography (silica gel, 0–10% 2M methanolic ammonia in dichloromethane) yielded (R)-2-benzyl-5-hydroxy-3-(1-methyl-2-pyrrolidinylmethyl)-1-phenylsulfonylindole (12.5 mg, 40%; HRMS-FAB$^+$ for $C_{27}H_{28}N_2O_3S$ calculated MH$^+$:461.18988; found MH$^+$:461.18724).

(b) (R)-5-Hydroxy-3-(1-methyl-2-pyrrolidinylmethyl)-1-phenylsulfonylindole: isolated as a side product from the above reaction (8.0 mg, 50%; HRMS-FAB$^+$ for $C_{20}H_{22}N_2O_3S$: calculated MH$^+$:371.14294; found MH$^+$:371.14078).

| Summary of Exemplified Compounds | | | | |
|---|---|---|---|---|
| $R^1$ | $R^2$ | $R^3$ | $R^{4b*}$ | Example # |
| Me | H | PhSO$_2$– | cyclohexyl-O– | 4 |
| Me | H | PhSO$_2$– | H | 5a |
| Me | H | 4-MeO-C$_6$H$_4$-SO$_2$– | H | 5b |
| Me | H | 4-F-C$_6$H$_4$-SO$_2$– | H | 5c |
| Me | H | PhSO$_2$– | Cl | 5d |
| Me | H | 4-MeO-C$_6$H$_4$-SO$_2$– | Cl | 5e |
| Me | H | 4-F-C$_6$H$_4$-SO$_2$– | Cl | 5f |
| Me | H | PhC(O)– | H | 5g |
| Me | H | 4-MeO-C$_6$H$_4$-C(O)– | H | 5h |
| Me | H | 4-F-C$_6$H$_4$-C(O)– | H | 5i |
| Me | H | 2-Cl-C$_6$H$_4$-C(O)– | cyclohexyl-O– | 5j |
| Me | H | 2-MeO-C$_6$H$_4$-C(O)– | cyclohexyl-O– | 5k |
| Me | H | 4-MeO-C$_6$H$_4$-C(O)– | cyclohexyl-O– | 5l |

-continued

Summary of Exemplified Compounds

| R¹ | R² | R³ | $R^{4b*}$ | Example # |
|---|---|---|---|---|
| Me | H | 3,4-methylenedioxyphenyl-C(O)— | cyclohexyl-O— | 5m |
| Me | H | 2,6-dichlorophenyl-C(O)— | cyclohexyl-O— | 5n |
| Me | H | thiophen-2-yl-C(O)— | cyclohexyl-O— | 5o |
| Me | H | phenyl-C(O)— | Cl | 5p |
| Me | H | 4-MeO-phenyl-C(O)— | Cl | 5q |
| Me | H | 4-F-phenyl-C(O)— | Cl | 5r |
| Me | H | MeS-C(S)-C(Me)< | cyclohexyl-O— | 6a |
| Me | H | 4-NC-phenyl-CH₂-S-C(S)-C(Me)< | cyclohexyl-O— | 6b |
| Me | H | phenyl-CH₂-S-C(S)-C(Me)< | cyclohexyl-O— | 6c |
| Me | H | MeS-C(S)-C(Me)< | Me | 6d |

-continued

Summary of Exemplified Compounds

| R¹ | R² | R³ | R⁴ᵇ* | Example # |
|---|---|---|---|---|
| Me | H | MeS-C(=S)-C(Me)< | F | 6e |
| Me | H | CH₂=CHCH₂-S-C(=S)-C(Me)< | F | 6g |
| Me | H | HC≡C-CH₂-S-C(=S)-C(Me)< | F | 6h |
| Me | H | MeS-C(=S)-C(Me)< | H | 6i |
| Me | H | PhCH₂-S-C(=S)-C(Me)< | H | 6j |
| Me | H | CH₂=CHCH₂-S-C(=S)-C(Me)< | H | 6k |
| Me | H | Ph-C(O)- | cyclohexyl-O- | 7a |
| Me | H | 4-Me-C₆H₄-SO₂- | cyclohexyl-O- | 7b |
| Me | H | 4-Me-C₆H₄-SO₂- | F | 7c |
| Me | H | Ph-C(O)- | Br | 7d |
| Me | H | Ph-SO₂- | PhCH₂-O- | 7e |

-continued

Summary of Exemplified Compounds

| $R^1$ | $R^2$ | $R^3$ | $R^{4b*}$ | Example # |
|---|---|---|---|---|
| Me | H | MeNH-C(O)-C(Me)< (α-methyl, methylaminocarbonyl group) | benzyloxy (PhCH$_2$O—) | 8 |
| Me | H | MeNH-C(O)-C(Me)< | OH | 9 |
| Me | H | phenyl-SO$_2$— | phenyl-O— | 11 |
| Me | Bn | phenyl-SO$_2$— | OH | 12a |
| Me | H | phenyl-SO$_2$— | OH | 12b |

$R^{4a}$, $R^{4c}$ and $R^{4d}$ are all H.

Example 13
Binding Affinity for the 5-HT$_6$ Receptor

All of the compounds of the invention were evaluated using cell types receptive specifically to the 5-HT$_6$ receptor (for cloning and characterization of the human 5-HT$_6$ receptor see Kohen, et al. J. Neurochemistry, 66, 1996: 47–56). The assay protocol generally entailed the incubation of membranes prepared from cells expressing the 5-HT$_6$ receptor with $^3$H-LSD. Increasing levels of the test compound were incubated with the radioligand and the membrane homogenates prepared from the recombinant cells. After a 60 minute incubation at 37° C., the incubation was terminated by vacuum filtration. The filters were washed with buffer and the filters were counted for radioactivity using liquid scintillation spectrometry. The affinity of the test compound for the 5-HT$_6$ receptor was determined by computer-assisted analysis of the data and determining the amount of the compound necessary to inhibit 50% of the binding of the radioligand to the receptor. Concentrations ranging from $10^{-11}$ M to $10^{-5}$ M of the test compound were evaluated. For comparison, the affinity of clozapine for the 5-HT$_6$ receptor (Ki ~3 nm) was used as a standard. All of the compounds of the invention exhibited affinity for the human 5-HT$_6$ receptor, with Ki's of not greater than 200 nM. Preferred compounds, those of examples 4, 5a–d, 5g, 5i–l, 5o–r, 7a, 7d, 10 and 12b, exhibited Ki's of not greater than 10 nM. Still more preferred are compounds, those of examples 4, 5d, 5p, 7c, 7e, and 7d, which exhibited Ki's of not greater than 1 nM. The compounds of the invention also bound to the human 5-HT$_6$ receptor in a selective manner, relative to the human 5-HT$_{2C}$ and 5-HT$_7$ receptors. That is, the compounds of the invention bound to the human 5-HT$_6$ receptor with at least a 2-fold greater affinity, relative to the human 5-HT$_{2C}$ and 5-HT$_7$ receptors. The compounds of examples 5k, 5n, 5d, 5j and 5r bound to the human 5-HT$_6$ receptor with at least a 36-fold greater affinity, relative to the human 5-HT$_{2C}$ and 5-HT$_7$ receptors. The compounds of examples 5k, 5d and 5j bound to the human 5-HT$_6$ receptor with at least a 100-fold greater affinity, relative to the human 5-HT$_{2C}$ and 5-HT$_7$ receptors.

Example 14
Effect of Compounds on the cAMP Response of Human 5-HT$_6$ Receptors

The antagonist (or agonist) property of compounds for human 5-HT$_6$ receptors was determined by testing their effect on cAMP accumulation in stably transfected HEK293 cells.

Binding of an agonist to the human 5-HT$_6$ receptor will lead to a increase in adenyl cyclase activity. A compound which is an agonist will show an increase in cAMP production and a compound which is an antagonist will block the agonist effect.

Cell Assay: Human 5-HT$_6$ receptors were cloned and stably expressed in HEK293 cells. These cells were plated in 6 well plates in DMEM/F12 media with 10% fetal calf serum (FCS) and 500 µg/mL G418 and incubated at 37° C. in a CO$_2$ incubator. The cells were allowed to grow to about 70% confluence before initiation of the experiment.

On the day of the experiment, the culture media was removed, and the cells were washed once with serum free medium (SFM). Two mL of SFM+IBMX media was added and incubated at 37° C. for 10 min. The media were removed and fresh SFM+IBMX media containing various compounds, and 1 µM serotonin (as antagonist) were added to the appropriate wells and incubated for 30 min. Following incubation, the media were removed and the cells were washed once with 1 mL of PBS (phosphate buffered saline). Each well was treated with 1 mL cold 95% ethanol and 5 mM EDTA (2:1) at 4° C. for 1 hour. The cells were then scraped and transferred into Eppendorf tubes. The tubes were centrifuged for 5 min at 4° C., and the supernatants were stored at 4° C. until assayed.

cAMP Measurement: cAMP content was determined by EIA (enzyme-immunoassay) using the Amersham Biotrak cAMP EIA kit (Amersham RPN 225). The procedure used is as described for the kit. Briefly, cAMP is determined by the competition between unlabeled cAMP and a fixed quantity of peroxidase-labelled cAMP for the binding sites on anti-cAMP antibody. The antibody is immobilized onto polystyrene microtitre wells precoated with a second antibody. The reaction is started by adding 50 μL peroxidase-labeled cAMP to the sample (100 μL) preincubated with the antiserum (100 μL) for 2 hours at 4° C. Following 1 hour incubation at 4° C., the unbound ligand is separated by a simple washing procedure. Then an enzyme substrate, tetramethylbenzidine (TMB), is added and incubated at room temperature for 60 min. The reaction is stopped by the addition of 100 μL 1.0 M sulphuric acid and the resultant color read by a microtitre plate spectrophotometer at 450 nM within 30 minutes.

All of the compounds of the invention which were tested in the above assays were found to be antagonists. The potency of compounds of the invention as antagonists is expressed as an $EC_{50}$, which is the concentration causing 50% inhibition of the serotonin-stimulated cAMP response. The table below presents the $EC_{50}$'s of some of the compounds of the invention compared to clozapine as a reference compound.

| Example # | $EC_{50}$ (M) |
| --- | --- |
| clozapine | $9.5 \times 10^{0}$ |
| 5j | $6.4 \times 10^{-8}$ |
| 5d | $8.4 \times 10^{-9}$ |
| 5r | $6.0 \times 10^{-9}$ |

We claim:

1. A compound according to Formula I or salt or hydrate thereof:

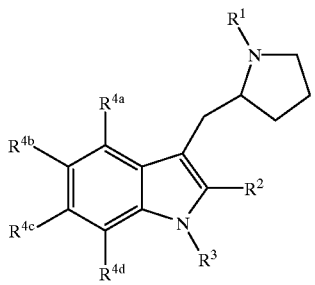

I wherein:
$R^1$ is selected from the group consisting of H and $C_{1-4}$alkyl;
$R^2$ is selected from the group consisting of H, $C_{1-4}$alkyl and benzyl;
$R^3$ is selected from the group consisting of $COR^5$, $SO_2R^5$, $CONHC_{1-4}$alkyl and $C(S)SR^6$;
$R^{4a}$ is selected from the group consisting of H, OH, halo, $C_{1-4}$alkyl and $C_{1-4}$alkoxy;
$R^{4b}$ is selected from the group consisting of H, hydroxy, halo, $C_{3-7}$cycloalkyloxy, $C_{1-4}$alkoxy, $C_{1-4}$alkyl, benzyloxy, phenoxy, trifluoromethyl, trifluoromethoxy and vinyl;

$R^{4c}$ is selected from the group consisting of H, OH, halo, $C_{1-4}$alkyl and $C_{1-4}$alkoxy;
$R^{4d}$ is selected from the group consisting of H, OH, halo, $C_{1-4}$alkyl and $C_{1-4}$alkoxy;
$R^5$ is selected from the group consisting of phenyl, and naphthyl which are optionally substituted with 1–4 substituents selected from $C_{1-4}$alkoxy, $C_{1-4}$alkyl, halo, nitro, trifluoromethyl, trifluoromethoxy, 1,2-methylenedioxy, $C_{1-4}$alkylcarbonyl, $C_{1-4}$alkoxycarbonyl and $C_{1-4}$alkylS—; and
$R^6$ is selected from $C_{1-4}$alkyl, allyl, propargyl and optionally substituted benzyl wherein the benzyl group is optionally substituted with 1–4 substituents selected from cyano, $C_{1-4}$alkyl and halo.

2. A compound according to claim 1, wherein $R^1$ is methyl.

3. A compound according to claim 1, wherein $R^2$ is H.

4. A compound according to claim 1, wherein $R^3$ is selected from $COR^5$.

5. A compound according to claim 4, wherein $R^5$ is selected from phenyl optionally substituted with 1–2 groups selected from methyl, methoxy, fluoro, chloro and 1,2-methylenedioxy.

6. A compound according to claim 5, wherein is $R^5$ selected from phenyl, p-methylphenyl, p-fluorophenyl, p-methoxyphenyl, o-chlorophenyl, and o-methoxyphenyl.

7. A compound according to claim 1, or a salt or hydrate thereof, wherein $R^3$ is $C(S)SR^6$.

8. A compound according to claim 7, or a salt or hydrate thereof, wherein $R^6$ is methyl.

9. A compound according to claim 1, wherein $R^{4a}$ and $R^{4c}$ are H, $R^{4d}$ is halo and and $R^{4b}$ is selected from H, fluoro, cyclohexyloxy, hydroxy, benzyloxy, phenoxy, chloro and methyl.

10. A compound according to claim 9, wherein $R^{4b}$ is selected from cyclohexyloxy, chloro and fluoro and $R^{4d}$ is H.

11. A compound according to claim 10, wherein $R^1$ is methyl and $R^2$ is H.

12. A compound according to claim 1, or a salt or hydrate thereof, which compound is selected from:
5-Cyclohexyloxy-3-(1-methyl-2-pyrrolidinylmethyl)-1-phenylsulfonylindole;
2-Benzyl-5-hydroxy-3-(1-methyl-2-pyrrolidinylmethyl)-1-phenylsulfonylindole;
5-Hydroxy-3-(1-methyl-2-pyrrolidinylmethyl)-1-phenylsulfonylindole;
3-(1-Methyl-2-pyrrolidinylmethyl)-1-phenylsulfonylindole;
1-(4-Methoxyphenylsulfonyl)-3-(1-methyl-2-pyrrolidinylmethyl)indole;
5-Chloro-3-(1-methyl-2-pyrrolidinylmethyl)-1-phenylsulfonylindole;
5-Chloro-1-(4-methoxyphenylsulfonyl)-3-(1-methyl-2-pyrrolidinylmethyl)indole;
5-Chloro-1-(4-fluorophenylsulfonyl)-3-(1-methyl-2-pyrrolidinylmethyl)indole;
1-Benzoyl-3-(1-methyl-2-pyrrolidinylmethyl)indole;
1-(4-Methoxybenzoyl)-3-(1-methyl-2-pyrrolidinylmethyl)indole;
1-(4-Fluorobenzoyl)-3-(1-methyl-2-pyrrolidinylmethyl)indole;
1-(2-Chlorobenzoyl)-5-cyclohexyloxy-3-(1-methyl-2-pyrrolidinylmethyl)indole;
5-Cyclohexyloxy-1-(2-methoxybenzoyl)-3-(1-methyl-2-pyrrolidinylmethyl)indole;
5-Cyclohexyloxy-1-(4-methoxybenzoyl)-3-(1-methyl-2-pyrrolidinylmethyl)indole;

5-Cyclohexyloxy-1-(3,4-methylenedioxybenzoyl)-3-(1-methyl-2-pyrrolidinylmethyl)indole;
5-Cyclohexyloxy-1-(2,6-dichlorobenzoyl)-3-(1-methyl-2-pyrrolidinylmethyl)indole;
1-Benzoyl-5-bromo-3-(1-methyl-2-pyrrolidinylmethyl)indole;
1-Benzoyl-5-chloro-3-(1-methyl-2-pyrrolidinylmethyl)indole;
5-Chloro-1-(4-methoxybenzoyl)-3-(1-methyl-2-pyrrolidinylmethyl)indole;
5-Chloro-1-(4-fluorobenzoyl)-3-(1-methyl-2-pyrrolidinylmethyl)indole;
5-Cyclohexyloxy-3-(1-methyl-2-pyrrolidinylmethyl)-1-(S-methylxanthyl)indole;
5-Cyclohexyloxy-3-(1-methyl-2-pyrrolidinylmethyl)-1-[S-(4-cyanobenzyl)xanthyl]indole;
5-Cyclohexyloxy-3-(1-methyl-2-pyrrolidinylmethyl)-1-(S-benzylxanthyl)indole;
5-Methyl-3-(1-methyl-2-pyrrolidinylmethyl)-1-(S-methylxanthyl)indole;
5-Fluoro-3-(1-methyl-2-pyrrolidinylmethyl)-1-(S-methylxanthyl)indole;
1-(S-Benzylxanthyl)-5-fluoro-3-(1-methyl-2-pyrrolidinylmethyl)indole;
1-(S-Allylxanthyl)-5-fluoro-3-(1-methyl-2-pyrrolidinylmethyl)indole;
5-Fluoro-3-(1-methyl-2-pyrrolidinylmethyl)-1-(S-propargylxanthyl)indole;
3-(1-Methyl-2-pyrrolidinylmethyl)-1-(S-methylxanthyl)indole;
1-(S-Benzylxanthyl)-3-(1-methyl-2-pyrrolidinylmethyl)indole;
1-(S-Allylxanthyl)-3-(1-methyl-2-pyrrolidinylmethyl)indole;
5-Cyclohexyloxy-3-(1-methyl-2-pyrrolidinylmethyl)-1-benzoylindole;
5-Cyclohexyloxy-3-(1-methyl-2-pyrrolidinylmethyl)-1-(4-methylphenylsulfonyl)indole;
5-Benzyloxy-3-(1-methyl-2-pyrrolidinylmethyl)-1-(N-methylcarboxamido)indole;
5-Hydroxy-3-(1-methyl-2-pyrrolidinylmethyl)-1-(N-methylcarboxamido)indole;
1-Phenylsulfonyl-5-hydroxy-3-(1-methyl-2-pyrrolidinylmethyl)indole; and
1-Phenylsulfonyl-5-phenoxy-3-(1-methyl-2-pyrrolidinylmethyl)indole.

13. A compound according to claim 1, or a salt or hydrate thereof, which compound is selected from:
5-Cyclohexyloxy-3-(1-methyl-2-pyrrolidinylmethyl)-1-phenylsulfonylindole;
2-Benzyl-5-hydroxy-3-(1-methyl-2-pyrrolidinylmethyl)-1-phenylsulfonylindole;
5-Hydroxy-3-(1-methyl-2- pyrrolidinylmethyl)-1-phenylsulfonylindole;
3-(1-Methyl-2-pyrrolidinylmethyl)-1-phenylsulfonylindole;
1-(4-Methoxyphenylsulfonyl)-3-(1-methyl-2-pyrrolidinylmethyl)indole;
5-Chloro-3-(1-methyl-2-pyrrolidinylmethyl)-1-phenylsulfonylindole;
5-Chloro-1-(4-methoxyphenylsulfonyl)-3-(1-methyl-2-pyrrolidinylmethyl)indole;
5-Chloro-1-(4-fluorophenylsulfonyl)-3-(1-methyl-2-pyrrolidinylmethyl)indole;
1-Benzoyl-3-(1-methyl-2-pyrrolidinylmethyl)indole;
1-(4-Methoxybenzoyl)-3-(1-methyl-2-pyrrolidinylmethyl)indole;
1-(4-Fluorobenzoyl)-3-(1-methyl-2-pyrrolidinylmethyl)indole;
1-(2-Chlorobenzoyl)-5-cyclohexyloxy-3-(1-methyl-2-pyrrolidinylmethyl)indole;
5-Cyclohexyloxy-1-(2-methoxybenzoyl)-3-(1-methyl-2-pyrrolidinylmethyl)indole;
5-Cyclohexyloxy-1-(4-methoxybenzoyl)-3-(1-methyl-2-pyrrolidinylmethyl)indole;
5-Cyclohexyloxy-1-(3,4-methylenedioxybenzoyl)-3-(1-methyl-2-pyrrolidinylmethyl)indole;
5-Cyclohexyloxy-1-(2,6-dichlorobenzoyl)-3-(1-methyl-2-pyrrolidinylmethyl)indole;
1-Benzoyl-5-bromo-3-(1-methyl-2-pyrrolidinylmethyl)indole;
1-Benzoyl-5-chloro-3-(1-methyl-2-pyrrolidinylmethyl)indole;
5-Chloro-1-(4-methoxybenzoyl)-3-(1-methyl-2-pyrrolidinylmethyl)indole;
5-Chloro-1-(4-fluorobenzoyl)-3-(1-methyl-2-pyrrolidinylmethyl)indole;
5-Cyclohexyloxy-3-(1-methyl-2-pyrrolidinylmethyl)-1-benzoylindole;
5-Cyclohexyloxy-3-(1-methyl-2-pyrrolidinylmethyl)-1-(4-methylphenylsulfonyl)indole;
1-Phenylsulfonyl-5-hydroxy-3-(1-methyl-2-pyrrolidinylmethyl)indole; and
1-Phenylsulfonyl-5-phenoxy-3-(1-methyl-2-pyrrolidinylmethyl)indole.

14. A compound according to claim 1, or a salt or hydrate thereof, which compound is selected from:
5-Cyclohexyloxy-3-(1-methyl-2-pyrrolidinylmethyl)-1-phenylsulfonylindole;
3-(1-Methyl-2-pyrrolidinylmethyl)-1-phenylsulfonylindole;
1-(4-Methoxyphenylsulfonyl)-3-(1-methyl-2-pyrrolidinylmethyl)indole;
5-Chloro-3-(1-methyl-2-pyrrolidinylmethyl)-1-phenylsulfonylindole;
5-Chloro-1-(4-methoxyphenylsulfonyl)-3-(1-methyl-2-pyrrolidinylmethyl)indole;
5-Chloro-1-(4-fluorophenylsulfonyl)-3-(1-methyl-2-pyrrolidinylmethyl)indole;
1-Benzoyl-3-(1-methyl-2-pyrrolidinylmethyl)indole;
1-(4-Methoxybenzoyl)-3-(1-methyl-2-pyrrolidinylmethyl)indole;
1-(4-Fluorobenzoyl)-3-(1-methyl-2-pyrrolidinylmethyl)indole;
1-(2-Chlorobenzoyl)-5-cyclohexyloxy-3-(1-methyl-2-pyrrolidinylmethyl)indole;
5-Cyclohexyloxy-1-(2-methoxybenzoyl)-3-(1-methyl-2-pyrrolidinylmethyl)indole;
5-Cyclohexyloxy-1-(4-methoxybenzoyl)-3-(1-methyl-2-pyrrolidinylmethyl)indole;
1-Benzoyl-5-bromo-3-(1-methyl-2-pyrrolidinylmethyl)indole;
1-(2-Chlorobenzoyl)-5-cyclohexyloxy-3-(1-methyl-2-pyrrolidinylmethyl)indole;
1-Benzoyl-5-chloro-3-(1-methyl-2-pyrrolidinylmethyl)indole;
5-Chloro-1-(4-methoxybenzoyl)-3-(1-methyl-2-pyrrolidinylmethyl)indole;
5-Chloro-1-(4-fluorobenzoyl)-3-(1-methyl-2-pyrrolidinylmethyl)indole;

5-Cyclohexyloxy-3-(1-methyl-2-pyrrolidinylmethyl)-1-benzoylindole;

5-Cyclohexyloxy-3-(1-methyl-2-pyrrolidinylmethyl)-1-(4-methylphenylsulfonyl)indole; and 1-Phenylsulfonyl-5-phenoxy-3-(1-methyl-2-pyrrolidinylmethyl)indole.

15. A compound according to claim 1, or a salt or hydrate thereof, which compound is selected from:

1-(2-Chlorobenzoyl)-5-cyclohexyloxy-3-(1-methyl-2-pyrrolidinylmethyl)indole;

5-Chloro-3-(1-methyl-2-pyrrolidinylmethyl)-1-phenylsulfonylindole; and

5-Chloro-1-(4-fluorobenzoyl)-3-(1-methyl-2-pyrrolidinylmethyl)indole.

16. A pharmaceutical composition, comprising a pharmaceutically acceptable carrier and, in an amount effective to antagonize the 5-HT$_6$ receptor, a compound of Formula I according to claim 1.

17. A pharmaceutical composition, comprising a pharmaceutically acceptable carrier and, in an amount effective to antagonize the 5-HT$_6$ receptor, a compound of according to claim 12.

18. A compound of claim 1, or a salt or hydrate thereof, wherein $R^3$ is $SO_2R^5$.

19. A compound of claim 1, or a salt or hydrate thereof, wherein $R^3$ is $CONHC_{1-4}$alkyl.

20. A compound of claim 19, or a salt or hydrate thereof, wherein $R^3$ is CONHmethyl.

21. A compound according to claim 14, or a salt or hydrate thereof, which compound is selected from:

5-chloro-3-(1-methyl-2-pyrrolidinylmethyl)-1-phenylsulfonylindole;

5-cyclohexyloxy-3-(1-methyl-2-pyrrolidinylmethyl)-1-phenylsulfonylindole;

3-(1-methyl-2-pyrrolidinylmethyl)-1-phenylsulfonylindole;

1-(4-methoxyphenylsulfonyl)-3-(1-methyl-2-pyrrolidinylmethyl)indole;

5-chloro-1-(4-methoxyphenylsulfonyl)-3-(1-methyl-2-pyrrolidinylmethyl)indole;

5-chloro-1-(4-fluorophenylsulfonyl)-3-(1-methyl-2-pyrrolidinylmethyl)indole;

5-cyclohexyloxy-3-(1-methyl-2-pyrrolidinylmethyl)-1-(4-methylphenylsulfonyl)indole; and 1-phenylsulfonyl-5-phenoxy-3-(1-methyl-2-pyrrolidinylmethyl)indole.

22. A compound according to claim 21, or a salt or hydrate thereof, which compound is selected from:

5-chloro-3-(1-methyl-2-pyrrolidinylmethyl)-1-phenylsulfonylindole; and 5-cyclohexyloxy-3-(1-methyl-2-pyrrolidinylmethyl)-1-phenylsulfonylindole.

23. A compound according to claim 22, or a salt or hydrate thereof, which compound is selected from:

5-chloro-3-(1-methyl-2-pyrrolidinylmethyl)-1-phenylsulfonylindole.

* * * * *